(12) United States Patent
Eyer et al.

(10) Patent No.: US 9,446,092 B2
(45) Date of Patent: Sep. 20, 2016

(54) USE OF A NEUROFILAMENT PEPTIDE FOR THE TREATMENT OF GLIOMA

(75) Inventors: Joël Eyer, Blaison-Gohier (FR); Alan Peterson, Westmount (CA); Julien Balzeau, Segre (FR); Raphaël Berges, Angers (FR)

(73) Assignees: UNIVERSITE D'ANGERS, Angers (FR); INSTITUT NATIONAL DE LA SANTE ET DE LA RECHERCHE MEDICALE (INSERM), Paris (FR); THE ROYAL INSTITUTION FOR THE ADVANCEMENT OF LEARNING/MCGILL UNIVERSITY, Montreal, Quebec (CA)

( * ) Notice: Subject to any disclaimer, the term of this patent is extended or adjusted under 35 U.S.C. 154(b) by 0 days.

(21) Appl. No.: 13/514,884

(22) PCT Filed: Dec. 14, 2010

(86) PCT No.: PCT/EP2010/069663
§ 371 (c)(1),
(2), (4) Date: Sep. 12, 2012

(87) PCT Pub. No.: WO2011/073207
PCT Pub. Date: Jun. 23, 2011

(65) Prior Publication Data
US 2013/0004429 A1    Jan. 3, 2013

Related U.S. Application Data

(60) Provisional application No. 61/286,207, filed on Dec. 14, 2009.

(30) Foreign Application Priority Data

Dec. 14, 2009 (EP) .................................. 09306227

(51) Int. Cl.
| A61K 49/00 | (2006.01) |
| G01N 33/574 | (2006.01) |
| G01N 21/64 | (2006.01) |
| A61K 38/16 | (2006.01) |
| A61P 35/00 | (2006.01) |

(52) U.S. Cl.
CPC ..................................... A61K 38/16 (2013.01)

(58) Field of Classification Search
USPC .......................................................... 514/101
See application file for complete search history.

(56) References Cited

U.S. PATENT DOCUMENTS

2009/0221476 A1*  9/2009  Bocquet et al. ................ 514/12

FOREIGN PATENT DOCUMENTS

FR    2 869 909    11/2005

OTHER PUBLICATIONS

ATCC T98G (ATCC CRL-1690).*
Rubenstein (Method Find Exp clin Pharmacol 1999, 21 (6):391).*
ATCC Tumor cell lines (2011, accessed Feb. 5, 2015).*
Cavaletti, G., et al., "Effect on the peripheral nervous system of the short-term intravenous administration of paclitaxel in the rat," Neurotoxicology, (1997), pp. 137-145, vol. 18, No. 1. (Abstract).
Jordan, M.A., et al., "Microtubules as a target for anticancer drugs," Nature Reviews Cancer, (2004), pp. 253-265, vol. 4, No. 4.
Louis, D.N., et al., "The 2007 WHO Classification of Tumours of the Central Nervous System," Acta Neuropathologica, (2007), pp. 97-109, vol. 114.
Dumontet, C., et al., "Mechanisms of Action of and Resistance to Antitubulin Agents: Microtubule Dynamics, Drug Transport, and Cell Death," Journal of Clinical Oncology, (1999), pp. 1061-1070, vol. 17, No. 3.
Gottesman, M.M., et al., "Biocheisry of Multidrug Resistance Mediated by the Multidrug Transporter," Annu Rev Biochem, (1993), pp. 385-427, vol. 62.
Heurtault, B., et al., "A Novel Phase Inversion-Based Process for the Preparation of Lipid Nanocarriers," Pharmaceutical Research, (2002), pp. 875-880, vol. 19, No. 6.
Hofer, S., et al., "Chemotherapy for malignant brain tumors of astrocytic and oligodendroglial lineage," J Cancer Res Clin Oncol, (2001), pp. 91-95, vol. 127.
Kaech, S., et al., "Culturing hippocampal neurons," Nature Protocols, (2006), pp. 2406-2415, vol. 1, No. 5.
McCarthy, K.D., et al., "Preparation of Separate Astroglial and Oligodendroglial Cell Cultures From Rat Cerebral Tissue," J Cell Biology, (1980), pp. 890-902, vol. 85.
Mollinedo, F., et al., "Microtubules, microtubule-interfering agents and apoptosis," Apoptosis, (2003), pp. 413-450, vol. 8, No. 5.
Ray, J., et al., "Proliferation, differentiation, and long-term culture of primary hippocampal neurons," Proc. Natl. Acad. Sci. USA, (1993), pp. 3602-3606, vol. 90.
Rocchetti, M., et al., "Predicting the active doses in humans from animal studies: A novel approach in oncology," European Journal of Cancer, (2007), pp. 1862-1868, vol. 43.
Wang, T-H., et al. "Paclitaxel-Induced Cell Death," Cancer, (2000), pp. 2619-2628, vol. 88, No. 11.
Bocquet et al., "Neurofilaments Bind Tubulin and Modulate Its Polymerization," The Journal of Neuroscience, vol. 29, No. 35, pp. 11043-11054, Sep. 2, 2009.

(Continued)

Primary Examiner — James H Alstrum Acevedo
Assistant Examiner — Tara Martinez
(74) Attorney, Agent, or Firm — Foley & Lardner LLP

(57) ABSTRACT

The present invention provides a new drug to treat malignant glioma, which is the most prevalent type of primary tumor of the central nervous system (CNS). The present invention indeed shows that the isolated NFL-TBS$_{40\text{-}63}$ peptide is highly specific for glioma cells, in which it triggers apoptosis. It is therefore presented here for use in a method for treating malignant glioma. The present invention further relates to the use of the NFL-TBS$_{40\text{-}63}$ peptide for detecting specifically glioma cells either in vivo, or in vitro, or for addressing chemical compounds to said tumor cells.

5 Claims, 15 Drawing Sheets

(56) References Cited

OTHER PUBLICATIONS

McGill, "Showcase Cancer: Novel Anti-Mitotic Peptides for the Treatment of Cancer," McGill University and the Research Institute of the McGill University Health Centre Technology Portfolio, Biotransfer, retrieved from the Internet: http://www.biotransfer.ca/portfolio_e.asp?id=2>, retrieved May 10, 2010.

McGill, "Novel Anti-Mitotic Peptides for the Treatment of Cancer," Technology Opportunity, Biotransfer, retrieved from the Internet: http://www.biotransfer.ca/portfolioMcGill-MUHC/04086_Peterson.pdf, retrieved May 10, 2010.

International Search Report issued in application No. PCT/EP2010/069663 on Apr. 26, 2011.

Betts et al., Amino Acid Properties and Consequences of Substitutions, in Bioinformatics for Geneticists, 2003, pp. 298-310.

Bryant et al., "A novel rat model for glioblastoma multiforme using a bioluminescent F98 cell line," Journal of Clinical Neuroscience, 2008, vol. 15, pp. 545-551.

Giard et al., "In Vitro Cultivation of Human Tumors: Establishment of Cell Lines Derived From a Series of Solid Tumors," Journal of the National Cancer Institute, Nov. 1973, vol. 51, No. 5, pp. 1417-1423.

Stein, "T98G: An Anchorage-independent Human Tumor Cell Line that Exhibits Stationary Phase G1 Arrest In Vitro," J. Cell. Physiol., 1979, vol. 99, pp. 43-54.

Taylor, "The Classification of Amino Acid Conservation," J. Theor. Biol.,1986, vol. 119, pp. 205-218.

Frank et al., "SPOT Synthesis: Epitope Analysis with Arrays of Synethic Peptides Prepared on Cellulose Membranes" Methods Mol. Biol., 1996, vol. 66, pp. 149-169.

Wolf, "Influence of matrigel on biodistribution studies in cancer research," Pharmazie, vol. 63, pp. 43-48, 2008.

Perego et al., "Invasive behaviour of glioblastoma cell lines is associated with altered organization of the cadherin-catenin adhesion system," Journal of Cell Science, vol. 115, pp. 3331-3340, 2002.

Wyrick et al., "Effects of Matrigel on the SF-767 malignant glioma athymic mouse tumor model," Anticancer Res., vol. 17, No. 4A, pp. 2419-2225, Jul./Aug. 1997.

American Type Culture Collection Standards Development Organization Workgroup ASN-0002, "Cell line misidentification: the beginning of the end," Nature Reviews, vol. 10, Jun. 2010, pp. 441-448.

ATCC, "Misidentified Cell Lines," 3 pages, accessed on Apr. 21, 2016 from http://www.atcc.org/Products/Cells_and_Microorganisms/Cell_Lines/Misidentified_Cell_Lines.aspx.

International Cell Line Authentication Committee (ICLAC), "Database of Cross-Contaminated or Misidentified Cell Lines," Version 7.2, Table 1, Publication date Mar. 10, 2014, 19 pages, accessed on Apr. 21, 2016 from http://standards.atcc.org/kwspub/home/the_international_cell_line_authentication_committee-iclac_/Cross_Contaminations_v7_2_2.pdf.

International Cell Line Authentication Committee, "ICLAC Database of Cross-Contaminated or Misidentified Cell Lines," 3 pages, accessed on Apr. 21, 2016 from http://iclac.org/databases/.

International Cell Line Authentication Committee, "The Role of ICLAC", 2 pages. accessed on Apr. 21, 2016 from http://standards.atcc.org/kwspub/home/the_international_cell_line_authentication_committee-iclac_/.

* cited by examiner

1 A

1 B

4 A

4 B

5A

5B

6A

6B

7 A

7 B

7 C

8 A

8 B

10 A

10 B

USE OF A NEUROFILAMENT PEPTIDE FOR THE TREATMENT OF GLIOMA

BACKGROUND OF THE INVENTION

Malignant gliomas are the most prevalent type of primary tumors of the central nervous system (CNS). The symptoms of a patient with glioblastoma depend on which part of the central nervous system is affected. A brain glioma can cause headaches, nausea and vomiting, seizures, and cranial nerve disorders as a result of increased intracranial pressure. A glioma of the optic nerve can cause visual loss. Spinal cord gliomas can cause pain, weakness, or numbness in the extremities. Gliomas do not metastasize by the bloodstream, but they can spread via the cerebrospinal fluid and cause "drop metastases" to the spinal cord.

High-grade gliomas are highly-vascular tumors and have a tendency to infiltrate. They have extensive areas of necrosis and hypoxia. Often tumor growth causes a breakdown of the blood-brain barrier in the vicinity of the tumor. As a rule, high-grade gliomas almost always grow back even after surgical excision.

Gliomas can not be cured. The prognosis for patients with high-grade gliomas is generally poor, and is especially so for older patients. Of 10,000 Americans diagnosed each year with malignant gliomas, only half are alive 1 year after diagnosis, and 25% after two years. Those with anaplastic astrocytoma survive about three years. Glioblastoma multiforme (GBM) has a worse prognosis.

Treatment for brain gliomas depends on the location, the cell type and the grade of malignancy. Often, treatment is a combined approach, using surgery, radiation therapy, and chemotherapy. The radiation therapy is in the form of external beam radiation or the stereotactic approach using radiosurgery. Spinal cord tumors can be treated by surgery and radiation. Temozolomide is a chemotherapeutic drug that is able to cross the blood-brain barrier effectively and is currently being used in therapy.

Glioblastomas are the most common primary CNS malignant glioma in adults, and account for nearly 75% of the cases. Although there has been steady progress in their treatment due to improvements in neuroimaging, microsurgery and radiation, glioblastomas remain incurable. Despite the combination of surgery, radiotherapy and chemotherapy, the median survival of patients with glioblastoma is limited to approximately one year, and the five-year survival rate following aggressive therapy including gross tumor resection is less than 10%. Glioblastomas cause death due to rapid, aggressive, and infiltrative growth in the brain. Failure of conventional treatments can be attributed to i) the precarious locations of the tumors within the brain, ii) the infiltrative nature of malignant gliomas that prevents the complete resection of all cancer cells, and iii) the lack of specificity of anti-tumor agents for neoplastic tissue that leads to severe neurotoxicity.

Therefore, there is still a need for an efficient anti-tumor drug that is able to treat gliomas, e.g. glioblastomas, without triggering neurotoxicity.

Among antitumor drugs, antimitotic agents represent an important class. Drugs, such as the taxane family, promote excessive stability of microtubules. In contrast, the Vinca alkaloids induce depolymerization of microtubules. By suppressing microtubule dynamics or functions, such drugs lead to the disruption of mitotic spindle function, the arrest of cell cycle progression, and eventually apoptosis (Mollinedo et al., 2003).

WO 2005/121172 described recently that small polypeptides, corresponding to the tubulin-binding site (TBS) and located in intermediate filament proteins (namely the neurofilament light chain protein NFL, keratine 8, GFAP, and vimentin) penetrate in tumor cells (e.g. MCF7, T98G, LS187, Cos, or NGP cells) where they disrupt the microtubule network and reduce their viability. More particularly, Bocquet et al (2009) showed that the second tubulin-binding site of the NFL protein (hereafter called "NFL-TBS.$_{40-63}$") is able to inhibit the proliferation of neuroblastoma and glioblastoma cell lines in vitro.

However, it was impossible, based on those results, to anticipate the behavior and activity of NFL-TBS.$_{40-63}$ in vivo, in particular on cell lines derived from malignant glioma.

Actually, it is well known that most of the chemotherapies based on microtubule-targeting drugs fail, for the two following main reasons: first, such drugs often result in the development of drug resistance, mediated by overexpression of transmembrane efflux pumps or the expression of tubulin isotypes and/or mutants that confer resistance (Dumontet et al., 1999). Second, they lack specificity for cancer cells and therefore induce unwanted toxicities (Mollinedo et al., 2003). Consequently, the use of microtubule-interacting agents has not been adapted for treating malignant gliomas that have a less than 20% response rate to conventional chemotherapy (Hofer et Herrmann, 2001) and for which existing treatments are commonly associated with debilitating toxic side effects (Cavaletti et al., 1997). A major challenge in the field of brain tumor was thus to identify an antitumoral agent which demonstrates therapeutic efficiency but a better specificity than the microtubule-targeting agents for brain tumour cells over normal tissue.

In this context, the Inventors have shown for the first time that a microtubule-depolymerizing peptide surprisingly demonstrates a unique specificity in vivo for glioma cells, thereby destroying their microtubule network and inhibiting their proliferation without obviously affecting the viability of the surrounding healthy cells.

The results presented below reveal that, when this peptide is injected by stereotaxy in rats bearing an intracranial F98 glioma, the size of the tumor is reduced by approximately 50%, and the health status of animals is significantly improved. Importantly, immunohistochemical staining revealed the presence of the peptide only in the tumor tissue, even 24 days after its injection, while it rapidly disappeared when injected into the same region of the brain in normal animals.

Together, these results demonstrate a selective uptake of the peptide used in the invention by glioma cells both in cell cultures and in animal models, where it significantly decreases their proliferation. Thus, it represents a promising tubulin-binding candidate for treating malignant gliomas.

SUMMARY OF THE INVENTION

In a first aspect, the present invention relates to an isolated amino acid sequence comprising the NFL-TBS$_{40-63}$ peptide (SEQ ID NO 1), or a biologically active derivative thereof, for use in a method for treating malignant glioma, preferably brain malignant glioma, more preferably glioblastoma multiform (GBM).

In a second aspect, the present invention relates to the use of an amino acid sequence comprising the NFL-TBS$_{40-63}$ peptide (SEQ ID NO 1), or a biologically active derivative thereof, for detecting glioma cells either in vivo, or in vitro.

In a particular embodiment, said method is a method for testing in vitro a biological sample for the presence or absence of malignant glioma cells, said method comprising:
a. Suspending the cells of the sample in an appropriate medium,
b. Mixing an amino acid sequence comprising the NFL-TB$_{40-63}$ peptide or a biologically active derivative thereof with the suspended cells of the sample,
c. Determining the percentage of cells containing said amino acid sequence, wherein the percentage of cells containing said amino acid sequence corresponds to the percentage of glioma cells in the sample.

In a preferred embodiment, said amino acid sequence is the NFL-TBS$_{40-63}$ peptide (SEQ ID NO 1) itself.

DETAILED DESCRIPTION OF THE INVENTION

Figure 1:
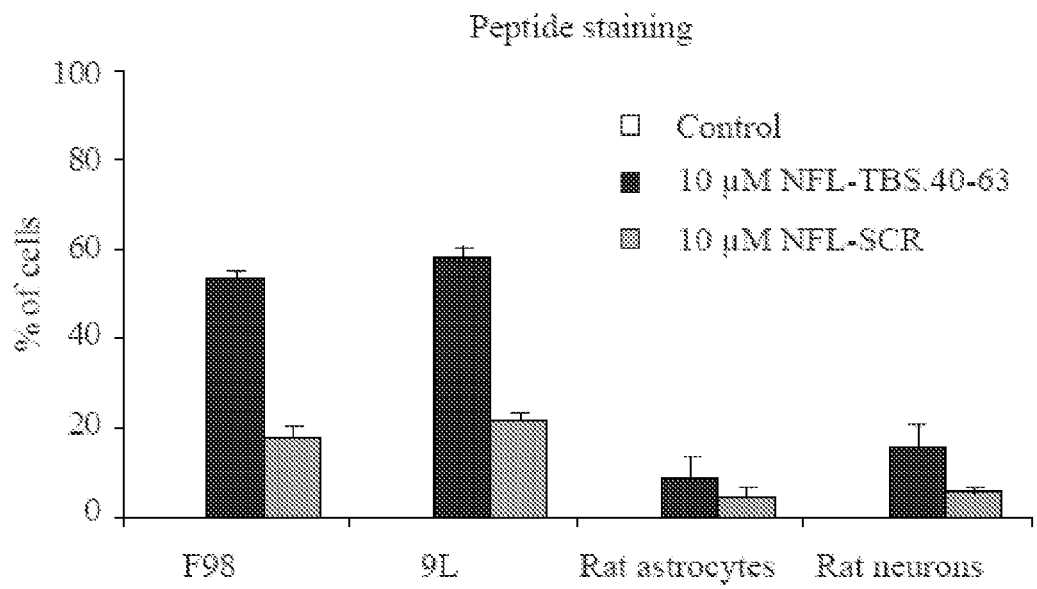
FIG. 1 demonstrates the in vitro specificity of the penetration of the NFL-TBS$_{40-63}$ peptide (10 µM, 6 h) in rat glioma cells (F98 and 9L), as compared to rat primary astrocytes and neurons, analyzed by immunohistochemistry (A). Cellular uptake of different doses of the NFL-TBS$_{40-63}$ peptide (1, 5, 10, 20, 50, 100 µM, 1 h, 37° C.) is further analyzed by flow cytometry (B).
Figure 1:
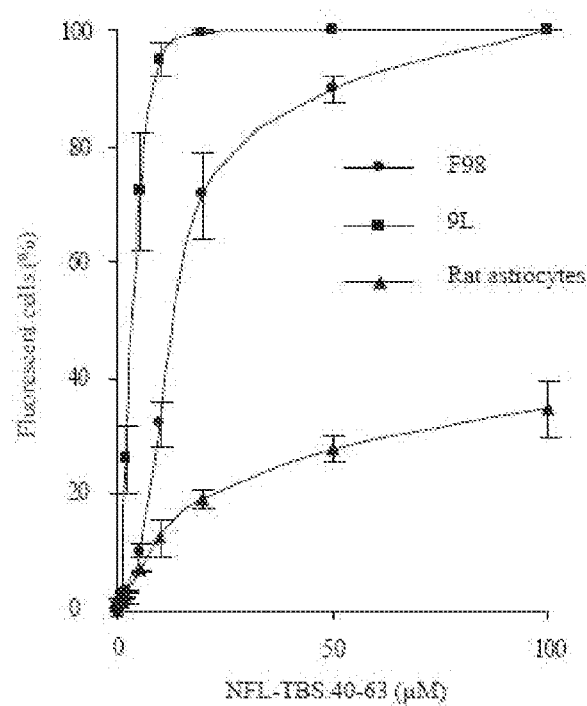

As mentioned previously, a major challenge in the field of brain tumours is to identify agents that have similar therapeutic efficiency as the microtubule-targeting agents but higher specificity for the brain tumour cells.

The present invention discloses the surprising selectivity of the microtubule-depolymerizing peptide NFL-TBS$_{40-63}$, which corresponds to the second tubulin-binding site of the light neurofilament subunit, as identified in Bocquet et al. (2009). This peptide has been shown previously i) to inhibit microtubule polymerization in vitro, ii) to penetrate in a human glioblastoma cell lineage (T98G) and, iii) to disrupt the microtubule cytoskeleton of these cells and to inhibit their proliferation (Bocquet et al., 2009).

The NFL-TBS$_{40-63}$ peptide is 24 amino acids long and has the following sequence: YSSYSAPVSSSLSVRRSYS-SSSGS (SEQ ID NO:1). In the context of the present application, it is referred to as the "peptide used in the invention". As mentioned previously, it corresponds to the second tubulin-binding site of the light neurofilament subunit (amino acids 40 to 63 of the TBS site of the NFL protein).

Surprisingly, the peptide used in the invention strongly affects the proliferation of glioma cells but has poor, if not undetectable, effects on normal astrocytes or neurons.

In contrast to traditional antimitotic agents such as taxol or Vinca alkaloids that enter cells by passive diffusion (Gottesman M M and Pastan I, 1993), the peptide used in the invention penetrates selectively in glioma cells. Both immunofluorescence microscopy and flow cytometry measures of peptide uptake revealed in vitro a preferential uptake by glioma cells when compared to astrocytes. Moreover, the saturable internalization demonstrated by FACS analysis, as well as the absence of internalization of the NFL-SCR scrambled peptide or D-amino acid peptide analogue, as well as the absence of internalization at 4° C. or in ATP-depleted conditions, all together argue for an active and selective transport of the NFL-TBS$_{40-63}$ peptide into glioma cells. This preferential uptake is also observable in vivo when the NFL-TBS$_{40-63}$ peptide is injected in the brain of animals bearing or not glioma. This selective tropism of the peptide for glioma cells when compared to other cells of the nervous system could be due to a selective expression of cell surface-expressed receptors by these cells. This unique property represents a major advantage of this peptide as compared with traditional microtubule destabilizing agents (i.e. taxanes or Vinca alkaloids), because it results in its lack of toxicity for other cells of the nervous system.

Therefore, in a first aspect, the present invention provides an isolated amino acid sequence comprising the NFL-TBS$_{40-63}$ peptide (SEQ ID NO:1), or a biologically active derivative thereof, for use in a method for treating malignant gliomas.

More precisely, in this aspect, the present invention relates to the use of an isolated amino acid sequence comprising the second tubulin-binding site of the light neurofilament subunit (namely NFL-TBS$_{40-63}$ (SEQ ID NO 1)) or a biologically active derivative thereof for the manufacture of a pharmaceutical composition for treating malignant glioma.

The isolated amino acid sequence of the invention yet comprises the NFL-TBS$_{40-63}$ peptide but cannot be the entire neurofilament light subunit itself, because this protein has not the same biologic activity as its fragment (i.e. the NFL-TBS$_{40-63}$ peptide). In particular, the entire NFL protein is not able to penetrate into glioma cells and has no antiproliferative activity onto these cells. The isolated amino acid sequence of the invention yet comprises the NFL-TBS$_{40-63}$ peptide provided that it is not the entire neurofilament light (NFL) subunit itself.

In general, the isolated amino acid sequence comprises no more than 100 amino acids, preferably 50 amino acids.

In a preferred embodiment, the isolated amino acid sequence of the invention consists of the NFL-TBS$_{40-63}$ peptide (SEQ ID NO 1) or a biologically active derivative thereof. Preferably, it consists of the NFL-TBS$_{40-63}$ peptide itself.

The present invention makes use of the "biologically active derivative of the NFL-TBS$_{40-63}$ peptide". As used herein, the term "peptide derivative" includes the variants and the fragments of the peptide to which it refers. Therefore, the "derivatives" of the second tubulin-binding site of the light neurofilament subunit (namely NFL-TBS$_{40-63}$ (SEQ ID NO 1)) include variants and fragments of the NFL-TBS$_{40-63}$ peptide. More particularly, in the context of the invention, the derivative designates "biologically active" variants and fragments of this peptide, i.e. variants and fragments retaining the biological activity and the specificity of the parent NFL-TBS$_{40-63}$ peptide. Thus, in the context of the invention, the "biologically active" derivatives of the NFL-TBS$_{40-63}$ peptide have to show a high biological capacity for inhibiting the proliferation of glioma cells, and have to show a high specificity toward the glioma tumoral cells of the brain, as the parent NFL-TBS$_{40-63}$ peptide. Preferably, the antiproliferative effect of the derivatives of the NFL-TBS$_{40-63}$ peptide on glioma cells has to be of at least about 70%, preferably between 80% and 90%, more preferably between 90% and 99%, and even more preferably 100% of the antiproliferative effect of the parent NFL-TBS$_{40-63}$ peptide, as assessed in vitro by conventional proliferation techniques. Also, the derivatives of the NFL-TBS$_{40-63}$ peptide have preferably the same specificity as the parent NFL-TBS$_{40-63}$ peptide toward glioma cells, as assessed in vitro by conventional cellular uptake experiments.

In a preferred embodiment, the derivative of the NFL-TBS$_{40-63}$ peptide is a biologically active fragment of the NFL-TBS$_{40-63}$ peptide. Said fragment comprises at least 12 successive amino acids of the parent NFL-TBS$_{40-63}$ peptide, preferably at least 16, more preferably at least 18 amino acids, and is characterized in that it retains the biological activity and specificity of the parent NFL-TBS$_{40-63}$ peptide.

In another preferred embodiment, the derivative of the NFL-TBS$_{40-63}$ peptide is a biologically active variant of the NFL-TBS$_{40-63}$ peptide. Said variant can be either an allelic variant of the peptide, or a peptidomimetic variant of the peptide. An "allelic variant of the peptide" has the same amino acid sequence as the NFL-TBS$_{40-63}$ peptide, except that one or more amino acids have been replaced by other amino acids or suppressed, the final peptide retaining the biological activity and specificity of the parent NFL-TBS$_{40-63}$ peptide. Preferably, such allelic variant has 70%, preferably 80%, more preferably 90% and even more preferably 95% of identity as compared with the parent NFL-TBS$_{40-63}$ peptide (SEQ ID NO1). For example, such allelic variant can be the TBS motif of the neurofilament light subunit of the quail (SEQ ID NO:3), which retains 20 over 24 amino acids of the NFL-TBS$_{40-63}$ peptide. The variant of the peptide can also be a peptidomimetic variant, which is an organic molecule that mimics some properties of the parent peptide, including at least one or more properties of interest that preferably is its biological activity. Preferred peptidomimetics are obtained by structural modification of peptides according to the invention, preferably using unnatural amino acids, D amino acid instead of L amino acids, conformational restraints, isosteric replacement, cyclization, or other modifications. Other preferred modifications include, without limitation, those in which one or more amide bond is replaced by a non-amide bond, and/or one or more amino acid side chain is replaced by a different chemical moiety, or one of more of the N-terminus, the C-terminus or one or more side chain is protected by a protecting group, and/or double bonds and/or cyclization and/or stereospecificity is introduced into the amino chain to increase rigidity and/or binding affinity. Still other preferred modifications include those intended to enhance resistance to enzymatic degradation, improvement in the bioavailability, and more generally in the pharmacokinetic properties, compared to the parent NFL-TBS$_{40-63}$ peptide. All of these variations are well known in the art. Thus, given the peptide sequences of the NFL-TBS$_{40-63}$ peptide, those skilled in the art are enabled to design and produce peptidomimetics having biological characteristics similar to or superior to such peptides. Preferred peptidomimetic variants of the NFL-TBS$_{40-63}$ peptide retain at least the biological activity and specificity of the NFL-TBS$_{40-63}$ peptide.

The peptides used in the invention (namely the amino acid sequence comprising the NFL-TBS$_{40-63}$ peptide or its fragments, its peptidomimetic or allelic variants) can be conveniently synthesized using art recognized techniques.

As used herein, "percentage of identity" between two amino acid sequences denotes the percentage of amino acids residues that are identical between the two sequences to be compared, obtained after the best alignment (optimum alignment), this percentage being purely statistical and the differences between the two sequences being distributed randomly and along their entire length. Sequence comparisons between two amino acid sequences can be performed for example with the BLAST program available on the website http://www.ncbi.nlm.nih.gov/gorf/b12.html, the parameters used being those given by default (in particular for the parameters "open gap penalty":5 and "extension gap penalty":2, the matrix selected being for example the "BLOSUM 62" matrix as suggested by the program, the percentage identity between the two sequences to be compared being calculated directly by the program).

In another embodiment, the present invention relates to a method of therapeutically treating malignant glioma by administering to a subject in need thereof an effective amount of a pharmaceutical composition comprising at least an isolated amino acid sequence comprising the NFL-TBS$_{40-63}$ (SEQ ID NO 1) or a biologically active derivative thereof.

Malignant gliomas are also known as high grade gliomas. They can affect the brain and the spinal cord. The therapeutic method of the invention is preferably dedicated to treat subjects carrying a brain malignant glioma, that is chosen among anaplastic astrocytoma (AA), glioblastoma multiform (GBM), anaplastic oligodendroglioma (AO) and anaplastic oligoastrocytoma (AOA), and, more preferably, carrying a glioblastoma multiform (GBM), as defined above.

In a preferred embodiment, said subject is a mammal, preferably a mouse, a rat, a cat, or a dog, and more preferably a human being.

Such pharmaceutical composition comprises an isolated amino acid sequence comprising the NFL-TBS$_{40-63}$ (SEQ ID NO 1) or a biologically active derivative thereof and a pharmaceutically acceptable carrier.

In a particular embodiment of the invention, the isolated amino acid sequence to be incorporated in the pharmaceutical composition of the invention is the NFL-TBS$_{40-63}$ peptide (SEQ ID NO 1) or a biologically active derivative thereof, and, preferably, the NFL-TBS$_{40-63}$ peptide itself.

In another embodiment, the peptide can be physically or chemically linked with a radioactive moiety, a cytotoxic component, or to an appropriate carrier (such as lipid nanocapsules as shown in example 3.4. below). The peptide of the invention would address these components specifically to the glioma cells, thereby compromising them.

For the purpose of the invention, suitable pharmaceutically acceptable carriers include, but are not limited to: water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, and polyvinyl pyrolidone. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, polyvinyl pyrollidone, sodium saccharine, cellulose, magnesium carbonate, etc. Some appropriate precise formulations are described, for example, in Remington, The Science and Practice of Pharmacy, 19th edition, 1995, Mack Publishing Company.

The pharmaceutical composition can be formulated in accordance with the routine procedures as a composition adapted for intravenous administration to an individual. Typically, compositions for intravenous administration are solutions in sterile isotonic aqueous buffer.

In a preferred embodiment the pharmaceutical composition of the invention is a liquid composition that is dedicated to be administered by intracerebral injection, and, more preferably, by intratumoral injection. Said intratumoral injection can be obtained for example by using stereotactic neurosurgery. This administration can be performed prior to or after a surgical operation intended to remove the brain tumor. In the first case, the composition enables to inhibit the growth of the tumor and avoid dissemination of the glioma cells and the occurrence of dramatic symptoms on the subject; in the second case, the composition can be used to destroy all the glioma cells that have not be removed during the surgical operation.

The effective dose of a compound according to the invention varies in function of numerous parameters such as, for example, the chosen administration method, the weight, age, sex, and the sensitivity of the individual to be treated. Consequently, the optimal dose must be determined individually, in function of the relevant parameters, by a medical specialist. In order to predict the expected active doses in human from the first animal studies presented hereunder, one can also use the $k_2$ and $C_T$ values as described by Rocchetti et al (2007).

It is foreseen that the effective doses for treating animals (for example rats) range between about 0.1 micromole and 5 milimole using a single stereotaxic injection (60 μl), preferably between about 0.2 and 0.5 micromoles. The human brain being in average 700 fold heavier than the rat brain, it is foreseen that the effective doses for treating human glioma will range between about 0.07 and 0.7 mmol, preferably between about 0.14 mmol and 0.35 mmol. These indicated doses are obviously to be adjusted in the context of clinical therapeutic studies.

As shown in the experimental part of the present application, the NFL-TBS$_{40-63}$ peptide is able to penetrate specifically into glioma cells, in vitro as well as in vivo. Therefore, before dying from apoptosis, the glioma cells are stained positively for the NFL-TBS$_{40-63}$ peptide in a specific manner, and can be identified among other healthy brain cells (in particular astrocytes and neurons). The NFL-TBS$_{40-63}$ peptide is thus a promising tool to detect glioma cells, either in vitro, or in vivo.

Therefore, in a second aspect, the present invention relates to the use of an amino acid sequence comprising the NFL-TBS$_{40-63}$ peptide (SEQ ID NO 1) or a biologically active derivative thereof for detecting glioma cells, preferably glioblastoma cells.

The characteristics of the intended amino acid sequence and of the biologically active derivative have been previously described.

In a preferred embodiment, said amino acid sequence is labeled so that it is easy to detect the presence or absence of the cells containing the peptide by conventional techniques.

The term "labeled" as used herein refers to any atom or molecule that can be used to provide a detectable (preferably quantifiable) effect, and that can be attached to an amino acid sequence. Labels include but are not limited to dyes, radiolabels such as $^{32}$P, binding moieties such as biotin, haptens such as digoxygenin, luminogenic, phosphorescent or fluorogenic moieties, mass tags; and fluorochromes alone or in combination with quenchers that can suppress or shift emission spectra by fluorescence resonance energy transfer (FRET). Said labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like, preferably by fluorescence. A label may be a charged moiety (positive or negative charge) or alternatively, may be charge neutral. Labels can include or consist of nucleic acid or protein sequence, so long as the sequence comprising the label is detectable.

Preferably, said labels are fluorochromes. Suitable fluorochromes include, for example:
1. fluorescein and derivatives, like hexachloro-fluorescein, tetrachloro-fluorescein, carboxyfluorescein (TAMRA), CAL FLUOR® (CAL Fluor Green 520, CAL FLUOR Gold 540, CAL FLUOR ORANGE 560, CAL FLUOR RED 590, CAL FLUOR RED 635 available from BIOSEARCH TECHNOLOGIES), succinimidyl ester of carboxyfluorescein (succinimidyl ester of 6-carboxy-2',4,4',5',7,7'-hexachlorofluorescein (HEX™) or succinimidyl ester of 6-carboxy-4',5'-dichloro-2',7'dimethoxyfluorescein (JOE™));
2. Rhodamine and derivatives, like 5- or 6-carboxy-X-rhodamine (ROX), N,N,N',N'-tetramethyl-6-carboxy-rhodamine;
3. Cyanine and derivatives like Cy3, Cy3.5, Cy5, Cy5.5;
4. BODIPY® chromophores like 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid;
5. Texas Red® and derivatives;
6. Pyrenetrisulfonic acid like APTS, HPTS (CASCADE BLUED); and
7. Eosin and derivatives.

More preferably, said fluorochrome is selected in the group comprising fluorescein and derivatives like hexachloro-fluorescein, tetrachloro-fluorescein, carboxyfluorescein (TAMRA), CAL FLUOR® (CAL Fluor Green 520, CAL FLUOR Gold 540, CAL FLUOR ORANGE 560, CAL FLUOR RED 590, CAL FLUOR RED 635 available from BIOSEARCH TECHNOLOGIES), succinimidyl ester of carboxyfluorescein (succinimidyl ester of 6-carboxy-2',4,4',5',7,7'-hexachlorofluorescein (HEX™) or succinimidyl ester of 6-carboxy-4',5'-dichloro-2',7'dimethoxyfluorescein (JOE™)).

In the context of the invention, preferred conventional techniques to detect such fluorochrome-labeled amino acid sequence include, but are not limited to, flow cytometry or fluorescence microscopy.

In a preferred embodiment, the amino acid sequence of the invention that is used to detect glioma cells consists of the NFL-TBS$_{40-63}$ peptide (SEQ ID NO 1) or a biologically active derivative thereof.

In a more preferred embodiment, the amino acid sequence of the invention is the NFL-TBS$_{40-63}$ peptide itself, which is coupled for example with a carboxyfluorescein dye or a biotin tag.

In another embodiment of the invention, the present invention relates to the use of the isolated amino acid sequence comprising the NFL-TBS$_{40-63}$ peptide or a biologically active derivative thereof for detecting the glioma cells in vivo, or, in other words, the isolated amino acid sequence comprising the NFL-TBS$_{40-63}$ peptide or a biologically active derivative thereof, for its use for detecting the glioma cells in vivo.

This can be particularly useful for the medical staff to estimate precisely the location of the tumor cells. Namely, glioma cells are generally not located in a confined area because they are able to infiltrate the surrounding regions of the original tumor. Moreover, the in vivo labeling of glioma cells could help surgeons to precisely determinate the frontier between tumor and healthy tissues so that they can remove more completely the tumor cells avoiding removing healthy tissues.

In this case, the amino acid sequence of the invention has to be administered prior to a surgical operation, for example one hour before, intracerebrally and preferably close to the tumor, so that it penetrates inside the tumor cells and guides the surgeon in removing all and only the tumor cells.

In this particular embodiment, the amino acid sequence of the invention is preferably labeled with fluorescent dyes or luminescent dyes, directly or through an appropriate carrier (such as nanocapsules), that can be detected in safe conditions during a surgical operation.

For example, the present invention provides a method for in vivo detecting the presence of malignant glioma cells, said method comprising:

a) labeling an amino acid sequence comprising the NFL-TBS$_{40-63}$ peptide or a biologically active derivative thereof with a fluorescent or luminescent dye, directly or through an appropriate carrier (such as nanocapsules), b) injecting said amino acid sequence intracerebrally prior to a surgical operation, c) applying, during surgery, a light of particular wavelength (depending on the fluorescent or luminescent dye) onto the tumor region in order to reveal the glioma cells.

In another particular embodiment, the present invention is related to the use of the isolated amino acid sequence comprising the NFL-TBS$_{40-63}$ peptide or a biologically active derivative thereof for detecting the glioma cells in vitro, for example for diagnosing a glioma or at least the presence of glioma cells into a biological sample.

For example, the present invention provides an in vitro method for testing a biological sample for the presence or absence of malignant glioma cells, said method comprising:

1. Suspending the cells of the sample in an appropriate medium,
2. Mixing an amino acid sequence comprising the NFL-TBS$_{40-63}$ peptide or a biologically active derivative thereof with the suspended cells of the sample,
3. Determining the percentage of cells containing said amino acid sequence thereof, wherein the percentage of cells containing said amino acid sequence corresponds to the percentage of glioma cells in the sample.

As used herein, the term "biological sample" or "sample" designates a cell culture that is handled in vitro. The cells in culture can be either of lineage origin or of primary origin. In this second case, the cells can be extracted from an animal brain following a biopsy or a surgical operation.

In the in vitro method of the invention, the percentage of cells containing said amino acid sequence "corresponds to" the percentage of glioma cells in the sample. This means that the percentage of cells containing the amino acid sequence used in the invention is equivalent to the percentage of glioma cells in the biological sample at more or less about 5%. When the absolute number of cells in the sample is known, one can also infer from the method of the invention the absolute number of glioma cells in the sample at more or less about 5%.

The cells are suspended and let grown in vitro in an appropriate medium. Such medium is well-known from a person skilled in art and comprises advantageously glucose and L-glutamine, fetal calf serum (e.g. 10%), and penicillin/streptomycin. The cells are conserved in a humidified incubator gassed with 5% $CO_2$ at 37° C.

In the first step of this method, the cells are suspended, e.g. by vortexing, so that the amino sequence of the invention can enter in contact with all the cells of the sample.

Preferably, the concentration of the amino acid sequence to be added is comprised between 1 and 200 µM, and more preferably between 2 and 150 µM, and even more preferably between 5 and 50 µM.

Preferably, the amino acid sequence is added on to the cells during at least 30 minutes, preferably 1 hour, and then the cells are washed extensively in order to remove the free remaining peptide.

In this method, the amino acid sequence to be added can be directly labeled with a dye or a conventional tag (e.g. biotin) as previously described, or can be coupled to appropriate carrier (such as nanocapsules). In this case, the analysis of the presence of the amino acid sequence is performed by usual means for detecting the dyes or tag in cellulo (e.g. flow cytometry, immunochemistry, etc. . . . as described in the following examples).

Alternatively, the amino acid sequence to be added is not labeled and its detection is performed indirectly by conventional means using for example antibodies against all or part of the amino acid sequence. In this case, conventional techniques of indirect detection can be used (e.g. flow cytometry, immunohistochemistry, Western Blot, etc. . . . ).

Preferably, the amino acid sequence of the invention is coupled to a fluorescent dye, directly or through an appropriate carrier, and the presence in the cells is revealed by flow cytometry (as explained in the following examples). More preferably, the fluorescent dyes are contained in lipid nanocapsules that are also coupled to the peptide of the invention.

In a preferred embodiment, the in vitro method of detection of glioma cells uses the NFL-TBS$_{40-63}$ peptide itself. More preferably, it uses a carboxyfluorescein-labelled NFL-TBS$_{40-63}$ peptide or a biotin-tagged NFL-TBS$_{40-63}$ peptide.

In another embodiment of the invention, the present invention relates to the use of the isolated amino acid sequence comprising the NFL-TBS$_{40-63}$ peptide or a biologically active derivative thereof for addressing or targeting chemical compounds to glioma cells in vitro or in vivo. In other words, the present invention relates to the isolated amino acid sequence comprising the NFL-TBS$_{40-63}$ peptide or a biologically active derivative thereof, for its use for addressing or targeting chemical compounds to the glioma cells in vivo. Also, the present invention discloses a method for addressing or targeting chemical compounds to glioma cells in vivo in a subject in need thereof, and a method for addressing or targeting chemical compounds to glioma cells in vitro.

Such chemical compounds can be directly coupled to the peptide of the invention, or can be contained in appropriate carriers (e.g. nanocapsules, liposomes, micelles, or any encapsulation mean that is known by the man skilled in the art) that are coupled to the peptide of the invention.

Said chemical compounds can be pharmaceutical compounds and/or labeling markers such as fluorescent molecules.

Said pharmaceutical compounds are preferably cytotoxic drugs, for example antimitotic drugs.

The chemical compounds are more preferably encapsulated in lipid nanocapsules as described below.

In a preferred embodiment, the in vitro and in vivo methods of targeting glioma cells use the NFL-TBS$_{40-63}$ peptide itself.

The following examples describe the high specificity and therapeutic efficiency of the NFL-TBS$_{40-63}$ peptide. They are however not limitative, in particular concerning the nature of amino acid sequence of the invention, and the experimental conditions to use it.

EXAMPLES

1. Materials

Biotinylated or carboxyfluorescein-labeled peptides corresponding to the labeled tubulin-binding site of NFL (NFL-TBS$_{40-63}$, SEQ ID NO:1) and the similarly labeled scrambled peptide (NFL-SCR, SEQ ID NO:2) were synthesized by Millegen (Toulouse, France), and dissolved in water at a concentration of 1 or 5 mM. In the NFL-TBS-biotin peptide, the biotin molecule is linked to the N-terminal end of the peptides. Also, the carboxyfluorescein molecule is linked to the N-terminal end of the peptides.

F98 and 9L glioma cell lines were obtained from ATCC (Manassas, Va., USA). Cells were grown in DMEM media with glucose and L-glutamine (Lonza France), containing 10% fetal calf serum (Lonza France), 1% penicillin/streptomycin (Sigma) in humidified incubator gassed with 5% $CO_2$ (37° C.) until reaching 80-90% confluence.

Rat primary astrocytes were obtained from cultures of cerebral cortex as originally described (McCarthy and de Vellis, 1980). Briefly, the cerebral cortex was dissected from newborn rats and cells were recovered after tissue homogenization, trypsination, and centrifugation. They were grown during 3 weeks in DMEM media with glucose and L-glutamine (Lonza France), containing 10% fetal calf serum (Lonza France), 1% penicillin/streptomycin (Sigma) in humidified incubator gassed with 5% $CO_2$ (37° C.).

Hippocampal neuronal cultures were prepared from newborn rat brains according to Ray et al. 1993 and Kaech and Banker 2006. Briefly, the hippocampi of animals younger than 2 days were recovered, minced and digested in 0.01% trypsin for one hour at 37° C. Dissociated cells were plated on coverslips precoated with 5 μg/ml poly-1-lysine and 7 μg/ml collagen at densities of $2 \times 10^5$/ml and incubated at 37° C. with a 5% CO2 atmosphere. Twenty-four hours later, the plating solution was replaced by B-27 neurobasal medium, and the second day cytosine arabinoside (20 μM) was added to eliminate non-neural cells. Experiments were performed 7 days after plating.

Human glioblastoma cell lines of U87-MG and T98G were obtained from ATCC (Manassas, Va., USA). GL261 mouse glioma cell line was kindly provided by Dr P Walker (Laboratory of Tumor Immunology, University Hospital Geneva, Switzerland). Human astrocytes were obtained from Lonza France. Purified newborn mouse primary astrocytes were obtained by the mechanical dissociation method from cultures of cerebral cortex as originally described (McCarthy and de Vellis, 1980).

Human glioblastoma cells, GL261 glioma cells and mouse primary astrocytes were grown in DMEM media with glucose and L-glutamine (Lonza France), containing 10% fetal calf serum (Lonza France), 1% penicillin/streptomycin (Sigma) in humidified incubator gassed with 5% $CO_2$ (37° C.) until reaching 80-90% confluence. Human astrocytes were cultured in Astrocyte Basal Medium (ABM) (Lonza) supplemented with the AGM SingleQuots growth factor (Lonza). Cells were maintained according to manufacturer's instructions.

Primary human glioblastoma cells obtained from tissue samples extracted in human brains during surgery are put in culture in a DMEM medium containing glucose, L-glutamine, 10% fetal calf serum, 10% penicillin/streptomycin (Sigma). Cells were plated (20 000 cells per $cm^2$) in MW96 and let grow at 37° C. in a humidified incubator gassed with 5% $CO_2$. The peptides and/or drugs are added 48 hours after their plating.

Lipid nanocapsules (LNC) were performed as previously described (Heurtault et al., 2002). Briefly, Solutol HS-15, Lipoid S75-3, sodium chloride, Labrafac CC and water were mixed by magnetic stirring (200 rpm) at room temperature leading to an oil/water emulsion. After heating, an interval of transparency at 70° C. can be observed, and the inverted phase "water in oil" is obtained at 85-87° C. Three temperature cycles alternating from 60 to 87° C. were applied, then before the last decrease of temperature, the mixture was diluted with 12.5 mL of cold water (close to 0° C.) and stirred for 15 min. DiD was added just before the last dilution. After LNC characterization, 369 μL of NFL-TBS2 (1 mM) were added to 1 mL of LNC (DiD) for peptide adsorption during 24 hours at 18° C. Then, a new characterization of LNC was performed.

2. Methods

2.1. Analysis of Cell Viability and Proliferation

The effects of peptides on the proliferation of glioma cells or astrocytes were evaluated by the MTS cytotoxicity assay and by counting directly the number of cells. For the MTS assay (Promega), 500 cells were seeded in 96-well plates, incubated at 37° C. for 24 hours, and treated by the peptide at the indicated concentrations for 24, 48 and 72 hours, or with vehicle (PBS or water). Media and peptides were replaced daily. Peptides were prepared in DMEM, and paclitaxel was dissolved in DMSO at a concentration of 2 mM and further diluted into DMEM. Viability was also determined by trypan blue staining. For manual counts, cells were treated with 0.25% trypsin/0.53 mM EDTA, centrifuged, and counted with a hemacytometer following addition of trypan blue dye. At each time, 3 to 6 wells per treatment were counted.

To assess cell proliferation, 5-bromodeoxyuridine (BrdU) immunohistochemistry was used. Cells were platted on coverslips and cultured in media containing biotinylated peptides (100 μM) for 72 hours, and incubated during 4 hours in the presence of 1 mg/mL BrdU (Sigma). Cells were then washed in PBS, fixed in 3% paraformaldehyde for 10 min and permeabilized with 1% Triton X-100 in PBS for 10 min. Cells were acidified to denature the DNA (2 N HCl, 10 min), neutralized (0.1 M sodium borate, 10 min) and then rinsed extensively in PBS. After blocking with 10% NGS (10 min) the cells were labeled with monoclonal anti-BrdU antibody (1/400) followed by Alexa 568 nm anti-mouse antibody (1/200). Nuclei were stained with 4'6-diaminido-2-phenylindole (DAPI; Sigma). The stained cells were observed with a Leica DMI6000 inverted microscope. Images were acquired with a CoolSNAP HQ2 camera and analyzed with Metamorph 7.1.7.0. software. Minimums of 200 cells were scored for BrdU incorporation, and experiments were repeated at least three times.

2.2. Cellular Uptake Analysis by Flow Cytometry

To evaluate the internalization of fluorescein-labeled NFL-TBS$_{40-63}$ peptide by FACS, glioma cells or astrocytes were seeded in 35 mm dishes and cultured for 1 hour at 37° C. in media containing fluorescein-labeled NFL-TBS$_{40-63}$ peptide at increasing concentrations or with vehicle (PBS). Cells were trypsinized, washed twice in cold PBS before incubation with trypsin (1 mg/mL) during 15 min at 37° C. To investigate a possible energy-dependant mechanism for the uptake of the peptide, cells were incubated at 4° C. with 20 μM fluorescein-labeled NFL-TBS2 peptide (after 15 min of 4° C. preincubation), or with 10 mM sodium azide in the presence of 6 mM 2-deoxy-D-glucose for 1 hour to deplete cellular ATP before addition of 20 μM fluorescence-labeled NFL-TBS2 peptide. Cells were then washed once, resuspended in 500 μl containing 50 μg/mL propidium iodide (Sigma, Saint-Quentin Fallavier, France), and analyzed with FACScalibur flow cytometer. Experiment on each cell type was repeated three times. 20,000 events per sample were analyzed in each experiment.

2.3. Cell Death Analysis by Flow Cytometry

To detect possible apoptotic processes, cells were seeded in 35 mm dishes and cultured in media containing biotinylated peptides (100 μM) or PBS alone for 72 hours. Paclitaxel (40 nM) was used as a positive control to induce apoptosis (Terzis et al., 1997). Cells were then trypsinized, washed in cold PBS, and stained with Annexin V-FITC (BD Pharmingen) in Annexin buffer for 15 min at room temperature. Finally, they were counterstained with 50 μg/mL propidium iodide (Sigma) and analyzed with a FACSCalibur flow cytometer. Experiment on each cell type was repeated three times. 20,000 events per sample were analyzed in each experiment.

2.4. Immunocytochemistry

Cells were plated on coverslips and cultured in media containing biotinylated peptides (10 μM) for 6 hours. Following PBS washing, the cells were fixed for 10 min in 4% paraformaldehyde, and washed 3 times in PBS. They were then incubated for 10 min in a 0.5% triton X-100 permeabilization solution, washed 3 times in PBS before incubation in a blocking solution (5% BSA) for 15 min. Glioma cells and astrocytes were incubated overnight at 4° C. with mouse anti-B-tubulin antibody (Sigma) 1/200, and neurons with mouse anti-BIII-tubulin antibody 1/200. Tubulin and biotinylated peptides were localized using respectively Alexa 568 nm anti-mouse antibody and streptavidin Alexa 488 nm (Molecular Probes) 1/200 for 1 hour, followed by washing in PBS. The preparations were counterstained with 3 µM 4'6-diaminido-2-phenylindole (DAPI; Sigma) for 5 min, and washed twice with PBS. Coverslips were mounted with an antifading solution.

Observations were carried out with an Olympus confocal microscope (BX50) using Fluoview.3.1. Software or a Leica DMI6000 inverted microscope. Images were acquired with a CoolSNAP-HQ2 camera and analyzed with Metamorph 7.1.7.0. software. Cells that are positive for peptide staining and cells with destroyed microtubule network were counted. Experiments on each cell type were repeated at least three times, and minimums of 200 cells were analyzed for each experiment.

2.5. Animal Studies 9 to 10 weeks old female syngeneic Fisher 344 rats were obtained from Charles River Laboratories France (L'Arbresle, France). The animals were housed in a temperature and humidity-controlled room with 12-hour on-off light cycles, and given free access to food and water.

All experimental procedures and animal care were carried out in conformity with the guidelines of the French Government and approved by the Regional Committee for Ethics on Animal Experiments.

Rat F98 cells at 70% confluency were trypsinized, counted on an hemacytometer, and checked for viability by trypan blue exclusion. Cells were washed twice in DMEM and a final suspension of $5 \times 10^4$ cells/mL in DMEM was obtained. Animals were anesthetized by intraperitoneal injection of a mixture of ketamine 10% (0.8 µg), and xylazine 2% (0.5 µg). Using a stereotaxic frame (David Kopf instruments, Tujunga, Calif., USA), a sagital incision was made through the skin to expose the cranium, and a small dental drill was used to make a burr hole in the skull 1 mm anterior and 2 mm lateral to the bregma. A volume of 10 µl of DMEM alone or containing 500 tumor cells was injected at a flow rate of 2 µl min using a 10-µl Hamilton syringe (Hamilton glass syringe 700 series RN) with a 32-G needle (Hamilton), at a depth of 4 mm deep from the outer border of the cranium into the striatum of the rat. The needle was left in place for an additional 5 min to avoid expulsion of the suspension from the brain, and then slowly withdrawn (0.5 mm/min).

Six days following glioma implantation, 60 µl infusions were performed at the coordinates of the tumor cells using a 10-µl Hamilton syringe with a 32-G needle. This syringe was connected to a 100-µl Hamilton 22-G syringe containing the peptide (Harvard Apparatus, Les Ulis, France) through a cannula (CoExTM PE/PVC tubing, Harvard Apparatus). Slow-infusion Convection-Enhanced Delivery procedure (CED) was performed with an osmotic pump (Harvard Apparatus) at a rate of 0.5 µl/min for 2 hours to achieve a total volume of 60 µl (Reference). After infusion, the needle was removed and the wound sutured.

Following intracerebral tumor cell implantation (day 0), rats were randomized into 4 groups. Six days post-implantation (day 6), the rats were treated by CED as follows: group 1: controls (60 µl of vehicle; n=10); group 2: 60 µl of 1 mM NFL-TBS$_{40-63}$ peptide (n=7); group 3: 60 µl of 1 mM NFL-SCR peptide (n=7); group 4: 60 µl of 5 mM NFL-TBS$_{40-63}$ peptide (n=7).

The animals were monitored each day for their clinical status (weight loss, ataxia, and periorbital hemorrhage) (Redgate et al., 1991). They were euthanized when affected by hemiplegia or at least 20% of weight loss. Animals were sacrificed at day 16, day 23, and day 30 (n=3/group) and their brain was removed, frozen in isopentane at −30° C., and stored at −80° C.

Frozen brains were serially sectioned using a Leica cryostat, and 20 µm sections were HE-stained for histomorphology and measure of the tumor volume. Images of HE-stained sections were captured with a Leica Z16APO macroscope using the Leica Application Suite 2.8.1 Software. The tumor area was manually outlined and measured using Image J software. Knowing the thickness and the number of sections, the total volume of each tumor was calculated. Tumor volumes were measured for three animals per group.

For immunohistochemistry, 12 µm sections were fixed with cold methanol during 10 min, washed 3 times in PBS, before blocking at room temperature for one hour with PBS 5% BSA. Sections were incubated with mouse anti-GFAP antibody (Sigma) 1/200 in PBS 5% BSA overnight, and then rinsed with PBS (3×5 minutes). GFAP and biotinylated peptides were localized using respectively anti-mouse antibody Alexa 568 nm and streptavidin Alexa 488 nm (Molecular Probes), diluted 1/200 in PBS 5% BSA for 90 minutes, followed by washing in PBS. The preparations were counterstained with 3 µM 4'6-diaminido-2-phenylindole (DAPI; Sigma) for 5 min and washed twice with PBS. Slides were mounted with an antifading solution and observed with a Leica DMR fluorescence microscope and the Leica IM500 software.

MRI and $^1$H-magnetic resonance spectroscopy: MRI was performed with a Bruker Avance DRX 300 (Germany) apparatus equipped with a vertical superwide-bore magnet of 7T. Qualitative T2-weighted images were obtained using rapid acquisition with relaxation enhancement (RARE) sequence (TR=2,000 ms; mean echo time (Tem)=31.7 ms; RARE factor=8; FOV=3×3 cm; matrix 128×128; nine contiguous slices of 1 mm, eight acquisitions). Magnetic resonance spectroscopy (MRS) was performed using a PRESS sequence with water suppression and cardiac triggering (Rapid Biomed GmbH, Germany). $^1$H spectra were acquired with the following parameters: TR/TE=1,500/11 ms; NEX=128; vowel size 27 µl (3×3×3 mm).

2.6. Statistical Analysis

Data are presented as mean S.E.M. (bars). Cell counting, cellular viability data, tumor volumes were analyzed by Student's t test using Prism version 3.00 (GraphPad Software, San Diego, Calif.). Asterisks indicate significant level vs. control*, $p<0.05$; , $p<0.005$; *, $p<0.0001$.

3. Results

3.1. Specificity of NFL-TBS$_{40-63}$ for Glioma Cells in Vitro

3.1.1. Specificity of the Penetration

To evaluate the specificity of NFL-TBS$_{40-63}$ (10 µM) on different cell types from the brain, its effects on rat F98 and 9L glioma cells, as well as primary cultures of rat astrocytes and neurons, was analyzed by immunofluorescence microscopy.

Image analysis and cell counting showed that more than 50% of the total cells contained detectable NFL-TBS$_{40-63}$ peptide (53.5%±1.5 for F98, and 58.2%±9 for 9L). At similar doses, the peptide penetrates much less in astrocytes (9%±4.6) or neurons (17.9%±5.9) (FIG. 1A).

Figure 2:
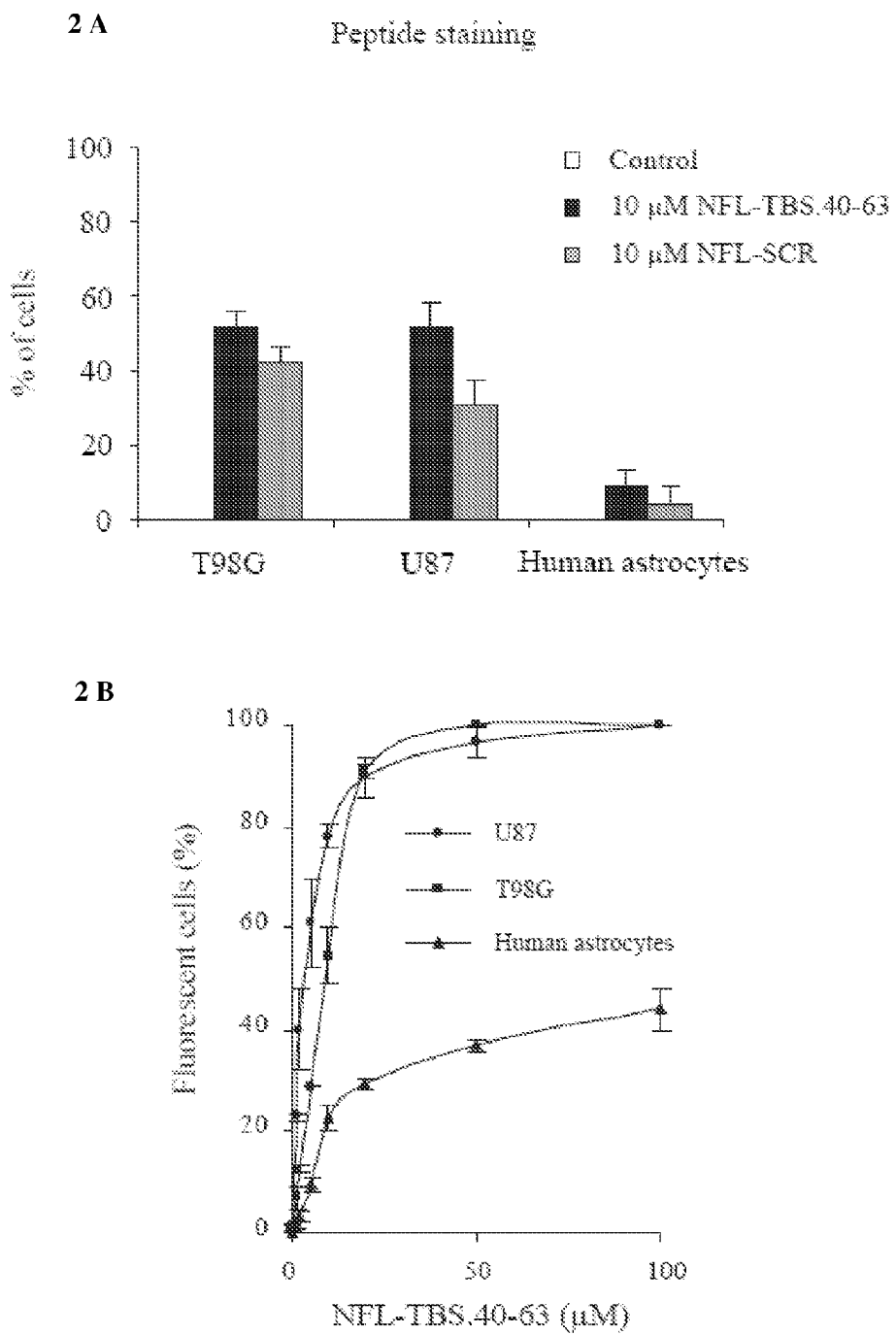
FIG. 2 demonstrates the in vitro specificity of the penetration of the NFL-TBS$_{40-63}$ peptide (10 µM, 6 h) in human glioma cells (U87-MG and T98G) as compared to normal human astrocytes, analyzed either by immunohistochemistry (A). Cellular uptake of different doses of the NFL-TBS$_{40-63}$ peptide (1, 5, 10, 20, 50, 100 µM, 1 h, 37° C.) is further analyzed by flow cytometry (B).
Figure 3:
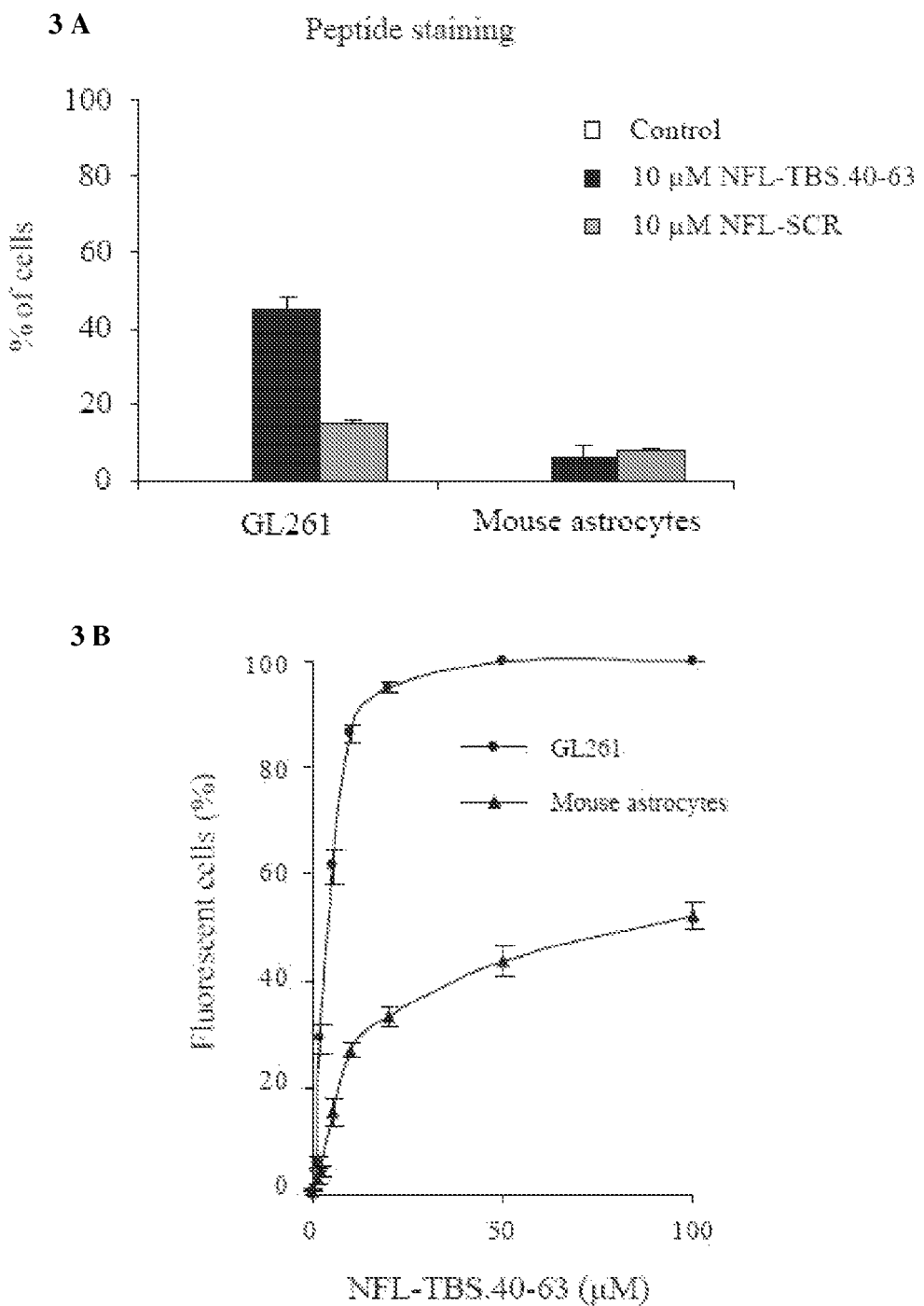
FIG. 3 shows the in vitro specificity of the penetration of the NFL-TBS$_{40-63}$ peptide (10 µM, 6 h) in mouse glioma cells (GL261) as compared to mouse astrocytes, analyzed either by immunohistochemistry (A). Cellular uptake of different doses of the NFL-TBS$_{40-63}$ peptide (1, 5, 10, 20, 50, 100 µM, 1 h, 37° C.) is further analyzed by flow cytometry (B).

Interestingly, similar results were obtained with human and mouse derived cells (FIG. 2A and FIG. 3A respectively).

Fluorescent-activated cell sorter (FACS) measurements were performed to further quantify cellular uptake of carboxyfluorescein-tagged peptides. To discriminate between membrane-bound and internalized fluorochrome, trypsin treatment of the cells before FACS analysis has been performed to avoid surface-binding of the peptide. Following incubation of the cells during 1 hour with 50 μM of peptide, 89.6%±2.5 of F98 and 100%±0 of 9L glioma cells contained the NFL-TBS$_{40-63}$ peptide, while only 28.0%±2.5 of astrocytes are positive (FIG. 1B).

These data show a preferential penetration of the NFL-TBS$_{40-63}$ peptide in rat glioma cells.

Interestingly; similar results were also obtained with human and mouse malignant glioma cells (FIG. 2B and FIG. 3B respectively).

Figure 13:
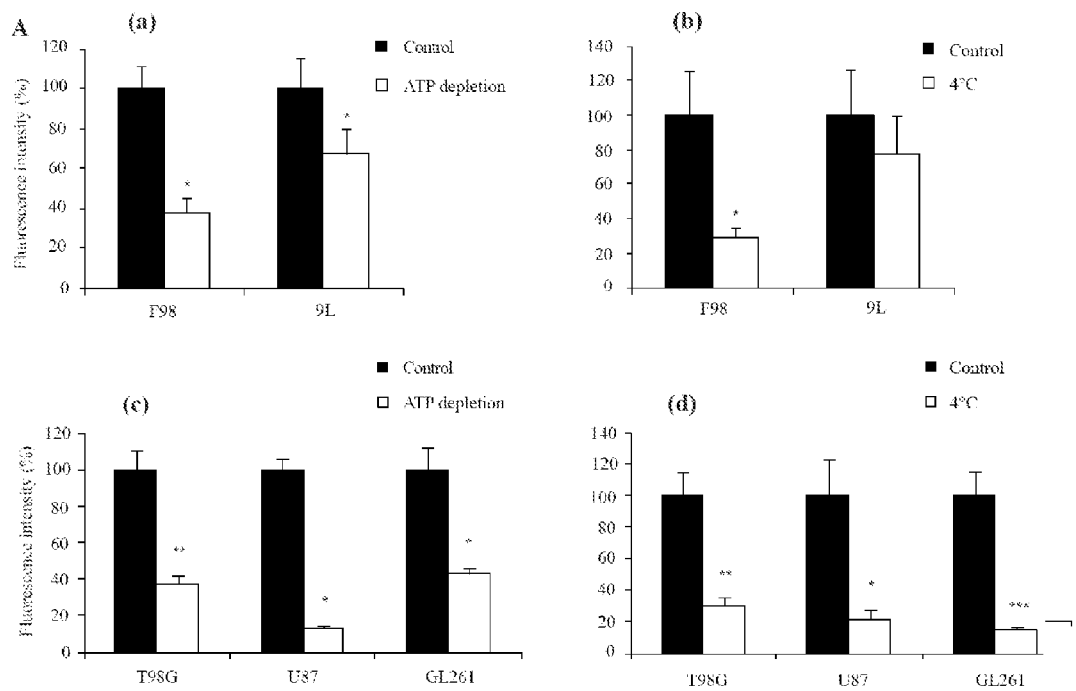
FIG. 13A shows that uptake of NFL-TBS$_{40-63}$ peptide is temperature and energy-dependant (A). (a) and (c): Glioma cells were incubated for 30 minutes at 37° C. in the presence of 20 µM fluorescein-tagged NFL-TBS$_{40-63}$ peptide. Intracellular ATP pool has been depleted (white columns) or not (black columns) by 30 minutes of preincubation with 10 mM sodium azide and 6 mM deoxyglucose. (b) and (d): Glioma cells were incubated 1 hour at 37° C. (black columns) or 4° C. (white columns) in the presence of 20 µM fluorescein-tagged NFL-TBS$_{40-63}$ peptide.
FIG. 13B shows that when T98G cells are treated with 10 µM of D-amino acid peptide analogue and analyzed by immunocytochemistry, internalization of peptide is strongly reduced.
Figure 13:
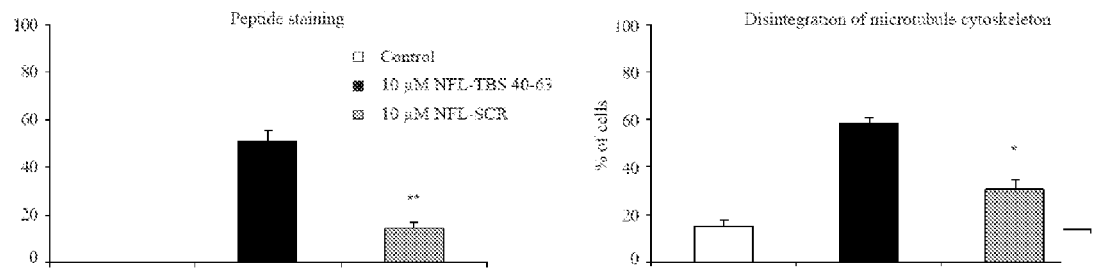

When glioma cells were incubated with the peptide at 4° C., or when ATP pool was depleted by preincubation of the cells with sodium azide and deoxyglucose, a significantly reduced uptake of NFL-TBS2 was observed indicating an energy dependant mechanism of internalization (FIG. 13A). Moreover, when T98G cells are treated with 10 μM of D-amino acid peptide analogue and analyzed by immunocytochemistry, internalization of peptide is strongly reduced, suggesting a receptor-mediated internalization by endocytosis (FIG. 13B).

Finally, the peptide also penetrates specifically in primary human glioblastoma cells isolated after surgery (data not shown).

All together, these in vitro results show importantly that the NFL-TBS$_{40-63}$ peptide penetrates specifically in glioma cells of human, rat, and mouse origin, in cell lineages as well as in primary glioma cells. On the contrary, these results point out that the NFL-TBS$_{40-63}$ peptide do not enter into the non tumoral cells present in the brain, that is astrocytes and neurons. This result will be further confirmed in the in vivo model of rats bearing F98 glioblastoma (see point 3.2. of the examples).

Figure 4:
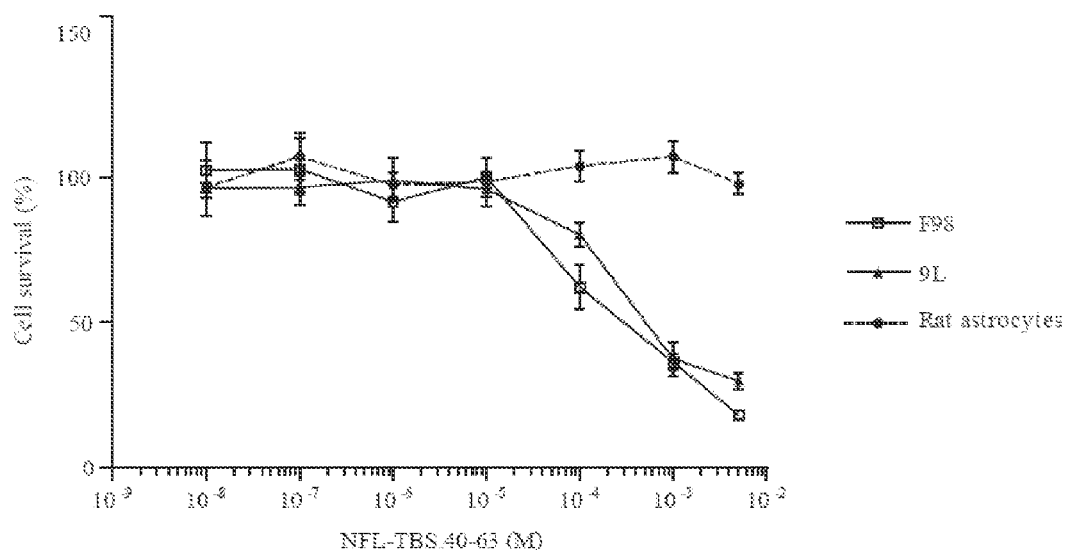
FIG. 4 shows the in vitro survival of rat glioma cells (F98 and 9L) and rat primary astrocytes in the presence of various concentration of NFL-TBS$_{40-63}$ peptide during 72 h assessed by the MTS assay (A). The microtubule cytoskeleton is completely disorganized in glioma cells but not in rat astrocytes and neurons, as assessed by immunohistochemistry (B).
Figure 4:
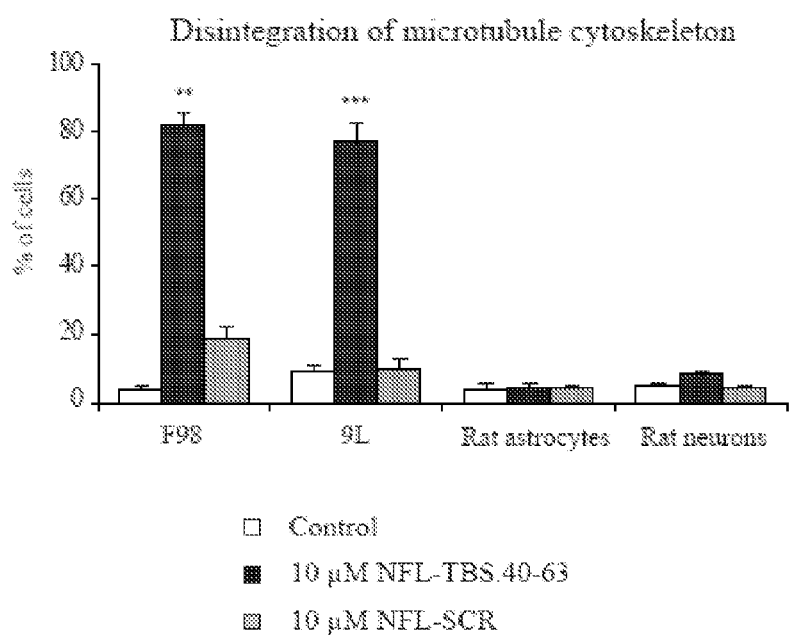

3.1.2. Reduced Viability of Malignant Glioma Cell in the Presence of NFL-TBS$_{40-63}$ Rat glioma cells (F98 and 9L) and astrocytes were treated with the NFL-TBS$_{40-63}$ peptide or its control scrambled sequence (NFL-SCR) at different concentrations (0, 20, 50 and 100 μM) and during different times (24, 48 and 72 hours). Taxol (40 nM) was used as a positive control for cytotoxicity. The MTS cytotoxicity assay, based on the capacity of viable cells to convert MTS to formazan by their mitochondrial dehydrogenase enzymes, was used. It was found that the cell viability of the two rat glioma cell lines was significantly reduced by 60.8%±2.8 for F98, and 30.0%±4.4 for 9L following 72 hours treatment with 100 μM of the NFL-TBS$_{40-63}$ peptide (FIG. 4A).

Figure 5:
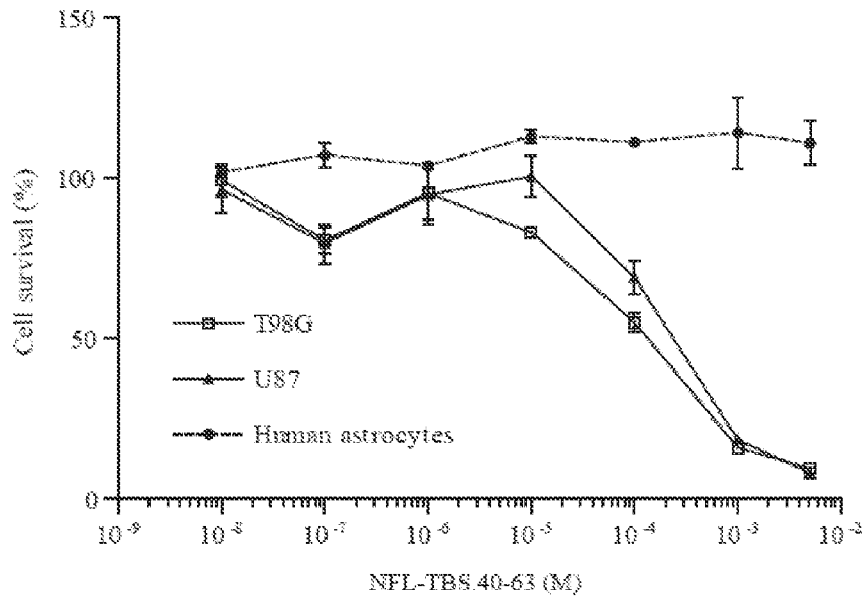
FIG. 5 shows the in vitro survival of human glioma cells (U87-MG and T98G) and human astrocytes in the presence of various concentration of the NFL-TBS$_{40-63}$ peptide during 72 h, assessed by the MTS assay (A). The microtubule cytoskeleton is completely disorganized in glioma cells but not in human astrocytes, as assessed by immunohistochemistry (B).
Figure 5:
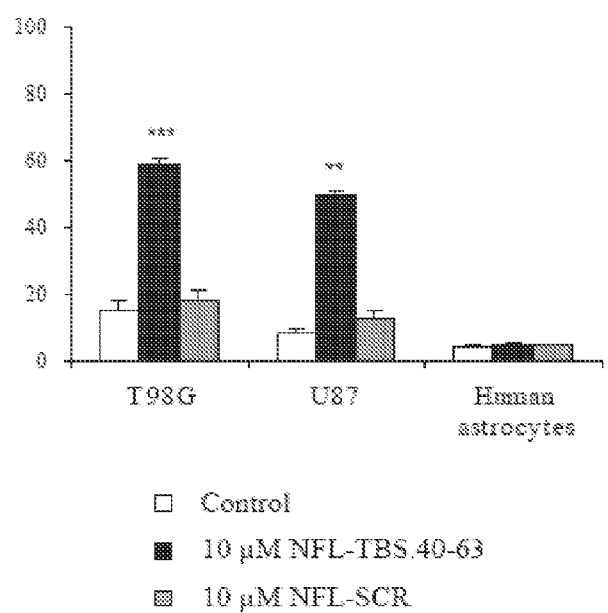
Figure 6:
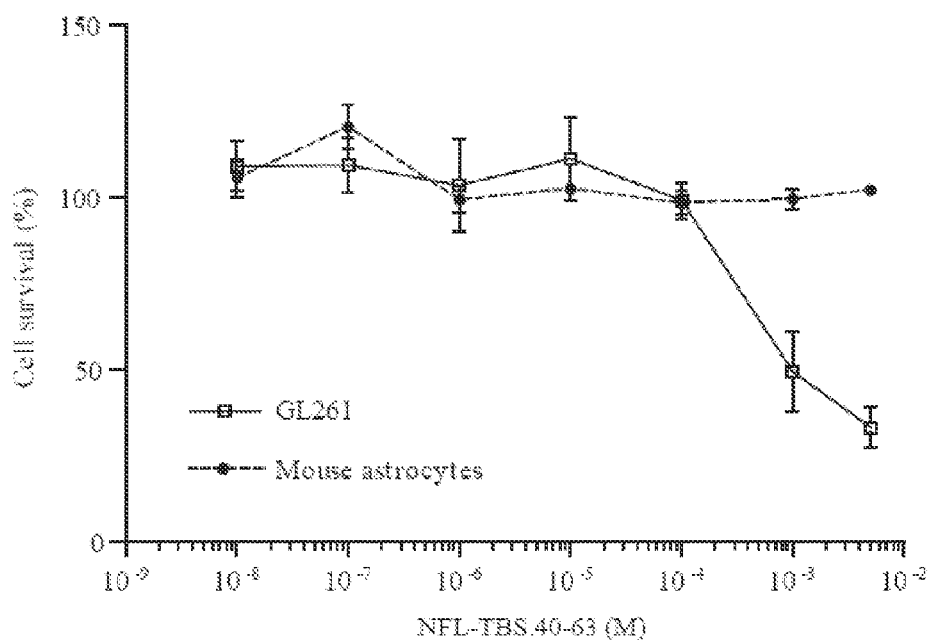
FIG. 6 shows the in vitro survival of the mouse glioma cells (GL261) and the mouse primary astrocytes in the presence of various concentration of NFL-TBS$_{40-63}$ peptide during 72 h, assessed by the MTS assay (A). The microtubule cytoskeleton is completely disorganized in glioma cells but not in mouse astrocytes, as assessed by immunohistochemistry (B).
Figure 6:
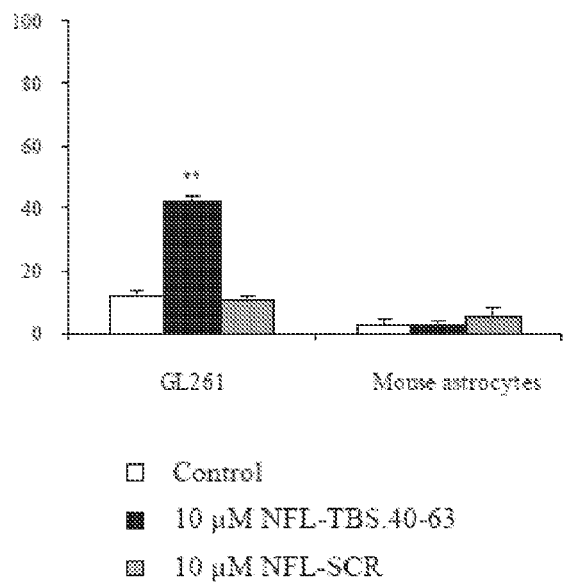

These results were reproduced using human and mouse malignant glioma cells (see FIGS. 5A and 6A respectively).

Figure 12:
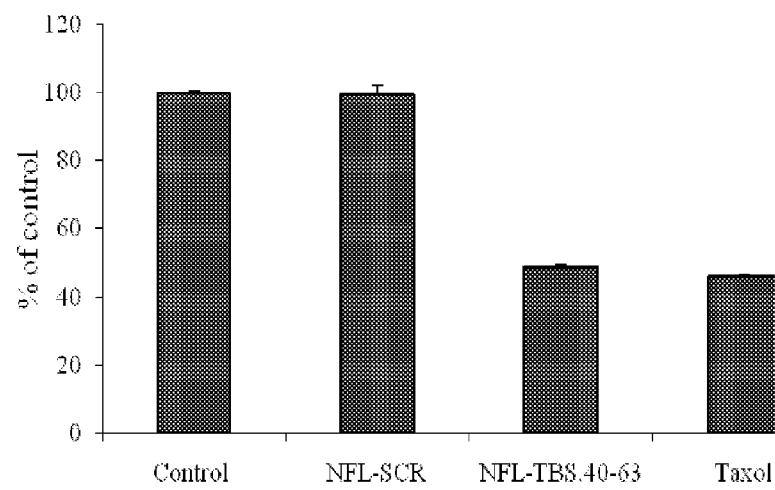
FIG. 12 shows the in vitro survival of primary human glioblastoma cells isolated after surgery in the presence of 100 µM NFL-TBS$_{40-63}$ peptide in comparison with 100 µM NFL-SCR peptide or 40 nM taxol during 72 h assessed by the MTS assay.

Moreover, the cell survival of primary human glioblastoma cells isolated after surgery is also greatly affected by the NFL-TBS40-63 peptide: after 72 hours of incubation with the NFL-TBS$_{40-63}$ peptide (100 μM), the cell survival is reduced by 50%. Interestingly, the cell survival is at the same level when the cells are treated with 40 nM of taxol, suggesting that the NFL-TBS$_{40-63}$ peptide has at least the same effect on cell viability than this well-known microtubule-depolymerizing drug (see FIG. 12).

Cell viability was also evaluated by Trypan blue dye exclusion test. This negatively charged chromophore only penetrates in cells when their membrane is damaged. In consequence, all cells that exclude the dye are viable. It has been observed that the NFL-TBS$_{40-63}$ peptide strongly affected the viability of rat, human and mouse gliomas, while astrocytes were not affected (data not shown).

To study the mechanism that potentially explains the reduced cell viability of the glioma cells in presence of the NFL-TBS$_{40-63}$ peptide, the microtubule cytoskeleton of these cells has been assessed by immunohistochemistry.

While untreated F98 and 9L cells were large and filled with a dense network of microtubules, those containing the NFL-TBS$_{40-63}$ demonstrated an atypical spherical shape with their tubulin co-aggregated with the intracytoplasmic peptide (not shown). Such alterations were observed in 82%±3 of total F98 cells and 76.7%±5.8 of total 9L cells. In contrast, the NFL-TBS$_{40-63}$ peptide only poorly affected astrocytes (4.7%±0.6), and neurons (8.5%±1.5). Moreover, the scrambled peptide NFL-SCR didn't alter the microtubule network of glioma cells, astrocytes and neurons (FIG. 4B). Similar results were obtained with human and mouse derived cells (FIGS. 5B and 6B respectively).

All together, these results show that the NFL-TBS$_{40-63}$ peptide destroys the microtubule cytoskeleton and reduces the viability of glioma cells, either from human, rat or mouse origin, whereas it does not affect the microtubule cytoskeleton and the viability of non tumoral cells that are also present in the brain, for example astrocytes and neurons. Importantly, this result has also been reproduced in vivo in non tumor-bearing (control) rats, in which the peptide had basically no effect and is rapidly eliminated (see 3.2. of the examples).

3.1.3. Specificity of the Anti Proliferative Effect

MTS assays and Trypan blue tests have shown that the NFL-TBS$_{40-63}$ peptide induced a decrease of the number of living cells. In order to determine whether this reduction reflects 1) a decrease of the cell proliferation (cytostatic effect), 2) a toxicity leading to cell death (cytotoxic effect), or 3) a combination of these two effects, the impact of peptide on the proliferation of the different cell types (rat glioma cell lines and astrocytes) was analyzed by measuring the incorporation of bromodeoxyuridine (BrdU), a thymidine analog, into DNA. This reveals the number of cells in S phase during the BrdU treatment and thereby the number of proliferating cells.

The treatment of rat glioma cells with 100 μM of NFL-TBS$_{40-63}$ peptide strongly decreased the incorporation of BrdU in these two lines examined (78.2%±3.0 inhibition of F98 cells, and 34.8%±2.6 of 9L cells) (FIG. 7A), indicating a lower number of proliferative cells. In strong contrast, a similar treatment of rat astrocytes did not affect their proliferation. Moreover, the NFL-SCR peptide has no effect on all these cells.

Figure 7:
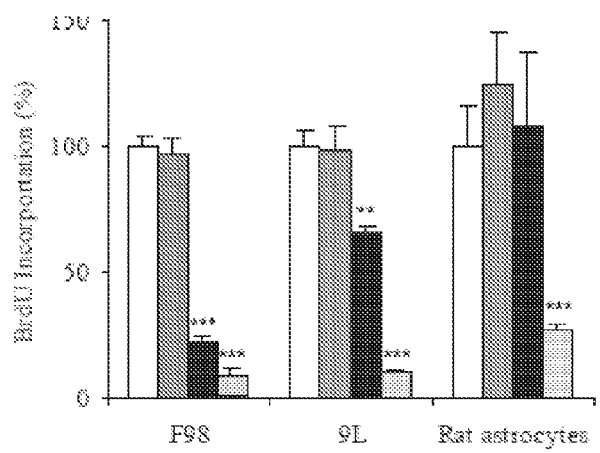
FIG. 7 shows the in vitro anti-proliferative activity of NFL-TBS$_{40-63}$ peptide (100 µM, 72 h) as compared with taxol (40 nM, 72 h), NFL-SCR (100 µM, 72 h) on rat cells (F98, 9L, astrocytes, A), human cells (U87, T98G, astrocytes, B), and mouse cells (GL261, astrocytes, C).
Figure 7:
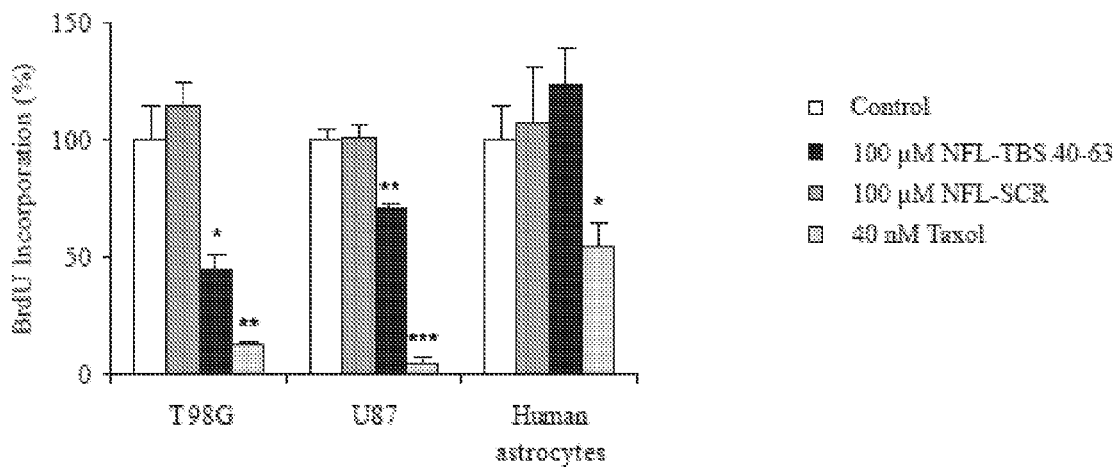
Figure 7:
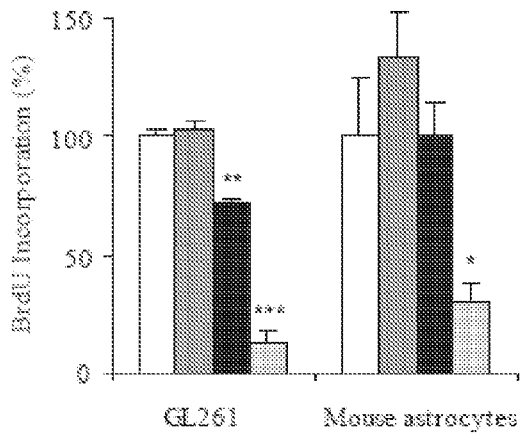

Similar results were obtained when cells derived from human and mouse were tested (FIGS. 7B and 7C respectively).

To conclude, these results show that the NFL-TBS$_{40-63}$ peptide reduces specifically the viability of glioma cells, either from human, rat or mouse origin. On the contrary, it does not affect the viability of non tumoral cells that are also present in the brain, for example astrocytes.

3.1.4. Specific Induction of Apoptosis in Malignant Glioma Cells

BrdU staining analysis demonstrated a cytostatic effect of the NFL-TBS$_{40-63}$ peptide on glioma cells. Microtubule-binding drugs are known to arrest proliferation and to induce cell death by apoptosis. To examine whether the decreased number of living glioma cells observed with the MTS assay and Trypan blue test was also associated with cell death (cytotoxic effect), F98, 9L glioma cells or astrocytes cells were incubated with 100 μM of the peptide during 72 hours, and then harvested and stained with propidium iodide (PI) and annexin V. Then, apoptosis quantification was evaluated by FACS analysis. Viable cells with intact membranes exclude PI, whereas the membranes of dead and damaged cells are permeable to PI. Moreover, the membrane phospholipid phopsphatidylserine (PS) is translocated from the inner to the outer leaflet of the external cellular environment in apoptotic cells, and thus Annexin V protein staining (which has a high affinity for PS and binds to cells with exposed PS) can be used to detect apoptotic cells.

Figure 8:
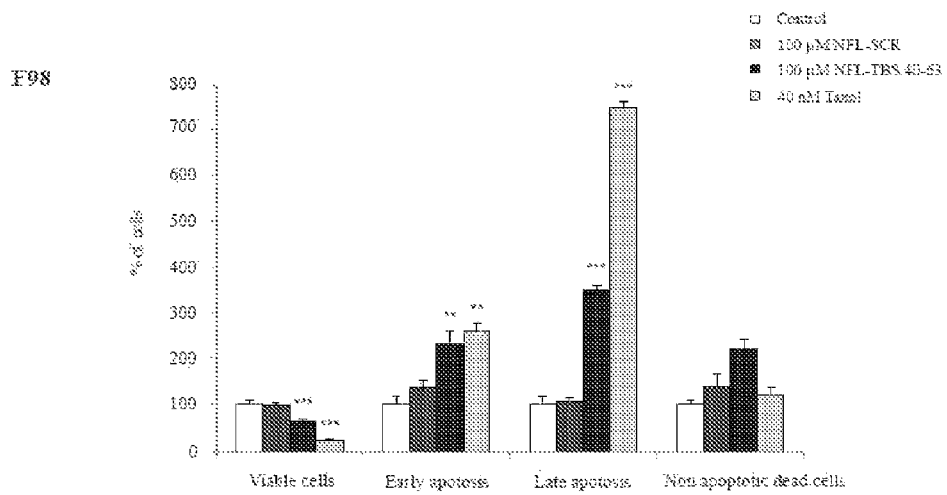
FIG. 8 reveals that the NFL-TBS$_{40-63}$ peptide (100 µM, 72 h) induces the in vitro apoptosis of rat glioma cells (A), of human and mouse glioma cells (B), but not of the corresponding astrocytes.
Figure 8:
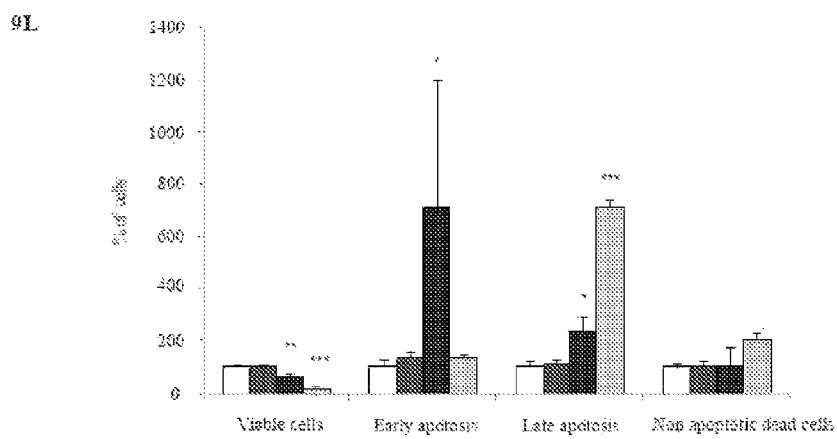
Figure 8:
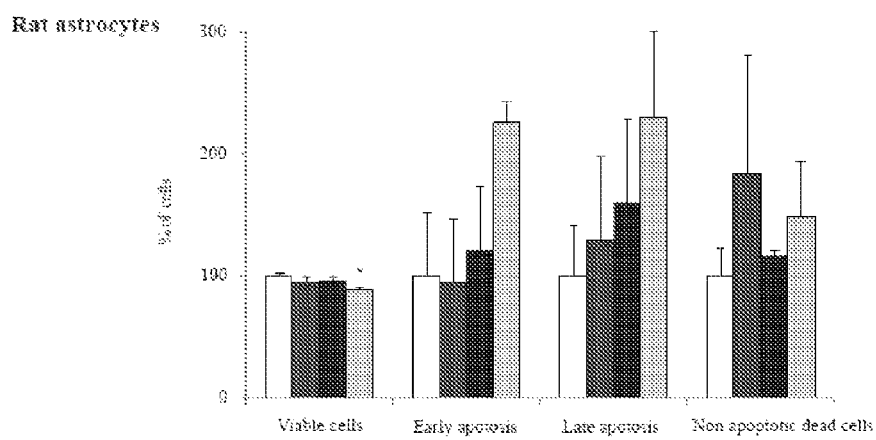
Figure 8:
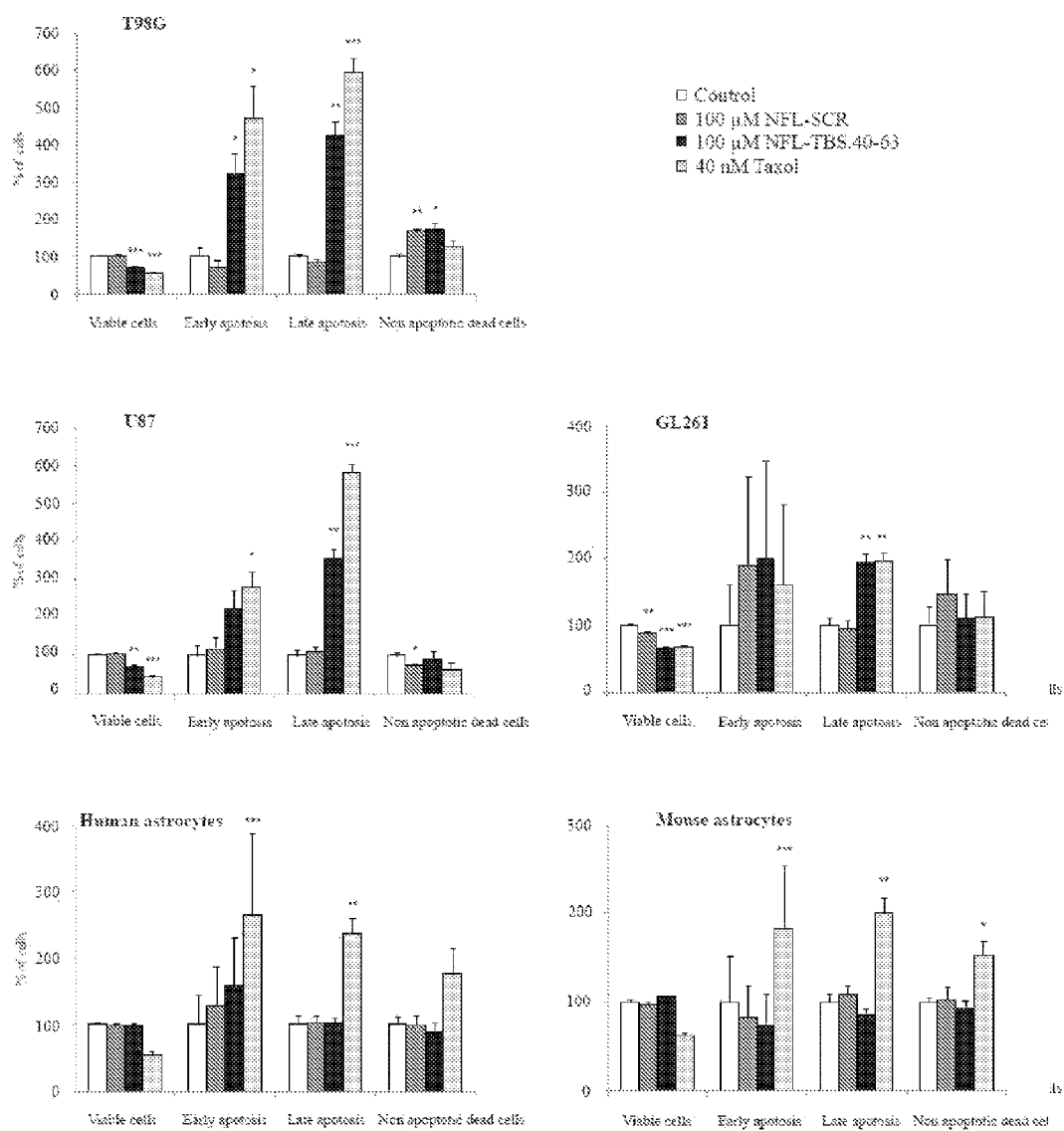

As shown in FIG. 8A, following NFL-TBS$_{40-63}$ treatment, the percentage of F98 cells in early or late apoptotic stage (which are considered as dead cells), was respectively 233.5%±43.3 and 347.7%±32.6 higher than negative control. Similarly, 9L cells displayed an increased number of early apoptotic (712.1%±581.3) and late apoptotic (233.6%±82.3) following such a treatment. Apoptotic response to NFL-TBS$_{40-63}$ peptide was correlated with the significant decrease of the living cell number in both F98 (−37.6%±5.0) and 9L (−32.6%±7.4) gliomas, in comparison with negative control. In contrast, primary astrocytes were not sensitive to NFL-TBS$_{40-63}$ peptide. At the same concentration, the NFL-SCR peptide has no effect on these different cell types.

Similar results were obtained when cells derived from human or mouse were tested (FIG. 8B).

To conclude, these results demonstrate that the inhibiting effect of the NFL-TBS$_{40-63}$ peptide on glioma cell proliferation is mediated by an active apoptosis mechanism, a cell death mechanism shared by various cancer cells, especially glioblastoma cells, when treated with antimitotic drugs (Wang et al., 2000). In other words, the NFL-TBS$_{40-63}$ peptide is therefore able to induce the death of glioma cells by apoptosis but has no effect on normal healthy brain cells.

3.2. Specificity of the Penetration of NFL-TBS$_{40-63}$ in Glioma Cells in Vivo Experiments in vitro showed a selective uptake of the NFL-TBS$_{40-63}$ peptide by glioma cells when compared to astrocytes or neurons. It was further tested whether the peptide could also target only tumor cells in vivo and inhibit selectively their proliferation using rats bearing F98 gliomas.

The F98 glioma was injected in the striatum by stereotaxy (day 0), and 6 days latter the animals were treated by intracerebral injection of 60 μL of 5 mM NFL-TBS$_{40-63}$ peptide (or vehicle). At days 16, 24 or 30, rats were euthanized and serial coronal sections of the brain were analyzed to detect the NFL-TBS$_{40-63}$ peptide and the glioma cells using anti-GFAP. Cell nuclei were also counterstained by DAPI.

Figure 9:
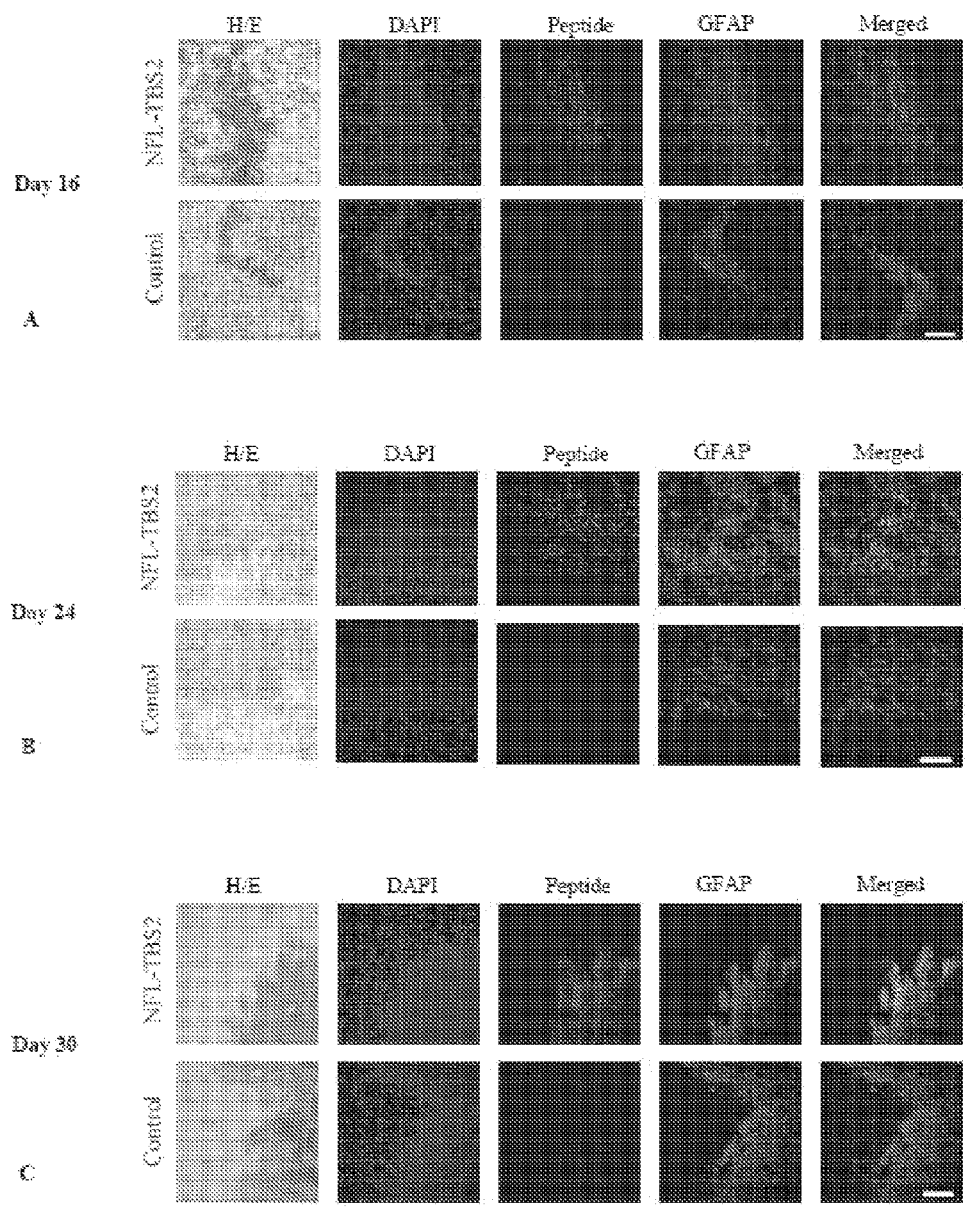
FIG. 9 shows that the injected NFL-TBS$_{40-63}$ peptide (5 mM/60 µL) selectively targets glioma cells pre-implanted in vivo in the brain of rats, as this peptide localized on the coronal sections only in the tumor cells, at day 16 (A), 24 (B), or 30(C).

As shown in the FIG. 9, the NFL-TBS$_{40-63}$ peptide (green fluorescence) was detected in glioma cells at each time point and not in the healthy surroundings cells (the peptide colocalizes with GFAP staining).

Importantly, when non tumor-bearing (control) rats were treated according to the same procedure, the NFL-TBS$_{40-63}$ peptide was rapidly eliminated and was not detectable at these time points. Moreover, no major cellular defects could be detected or associated to the presence of the peptide when injected in normal brain. In a physiological point of view, no clinical signs of distress, such as weight loss or hunched posture were noticed when these non tumor-bearing (control) rats were treated with the NFL-TBS$_{40-63}$ peptide.

All together these data indicate that the NFL-TBS$_{40-63}$ peptide penetrates specifically in glioma cells in vivo and avoids healthy cells. This is of particular interest, since this leads to the conclusion that the NFL-TBS$_{40-63}$ peptide has far less toxic side effects than the other microtubule-targeting drugs (e.g. paclitaxel, Cavaletti et al, 1997). To strengthen this, it has been shown that the NFL-TBS$_{40-63}$ peptide is indeed rapidly eliminated when it is injected in a normal brain, favoring a poor toxicity. This explains why, contrary to the other microtubule-targeting drugs, the microtubule-targeting NFL-TBS$_{40-63}$ peptide does not induce any apparent effect when injected in non tumor-bearing (control) rats.

3.3. Intracerebral Administration of NFL-TBS$_{40-63}$ Reduces Tumor Growth in Vivo To further test whether the NFL-TBS$_{40-63}$ peptide could also inhibit the growth of glioma implanted in rat, serial sections were stained with HE and the size of the tumor was evaluated by morphometry using ImageJ (see an example of coronal section on FIG. 10A).

Figure 10:
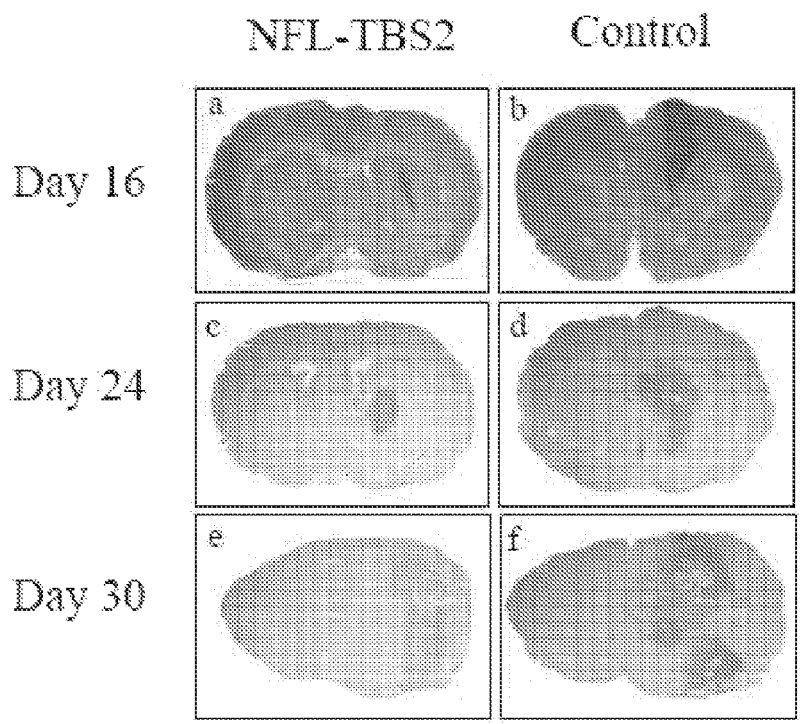
FIG. 10 shows the in vivo anti-proliferative effect of only one injection of the NFL-TBS$_{40-63}$ peptide (5 mM/60 µL) on the growth of pre-implanted glioma in rat brain at days 16, 24, and 30 on coronal sections (A). Quantification of the tumor volume calculated from the coronal sections in peptide-treated or control animals at days 16, 24 and 30 (B).
Figure 10:
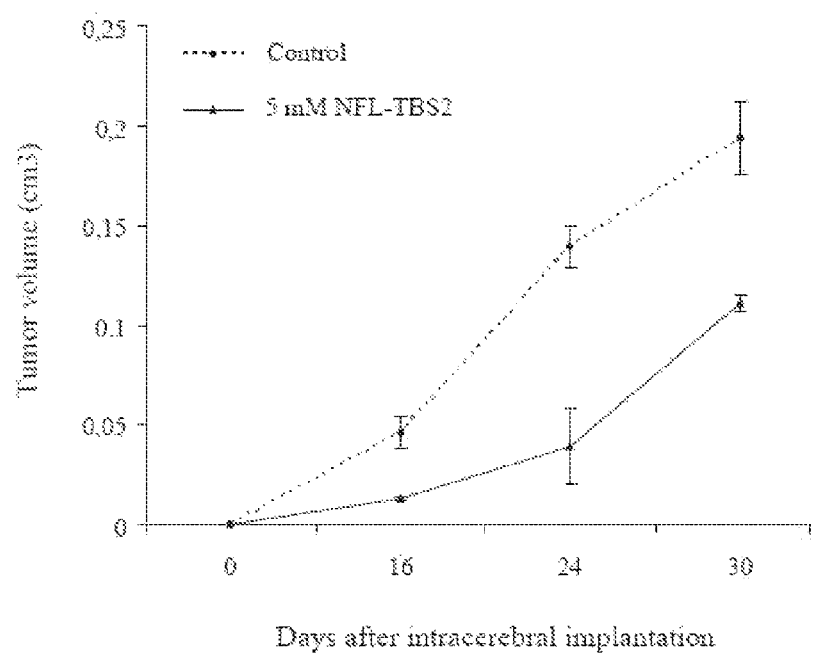

The animals treated with a single injection of the NFL-TBS$_{40-63}$ peptide exhibited significantly smaller tumors than those observed in untreated animals. As a matter of fact, the animals treated by the peptide exhibited a 71.7%±18.9 reduction of tumor volume (compared to vehicle treated animals) at day 16, a 72.0%±21.2 reduction at day 24, and a 42.8%±11.3 reduction at day 30 (FIG. 10B).

A similar tumor inhibition was also observed using MRI analysis on the same group of animals. The volume of this tumor is reduced in NFL-TBS$_{40-63}$ peptide-treated animals when compared to un-treated animals (not shown).

Figure 11:
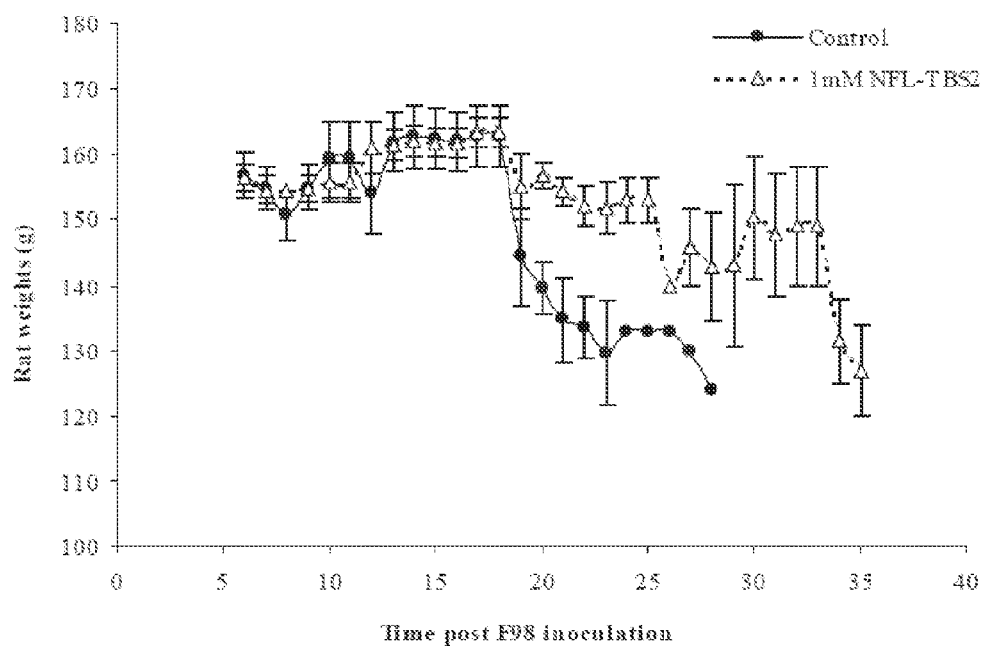
FIG. 11 demonstrates the therapeutical activity of only one injection of the NFL-TBS$_{40-63}$ peptide (5 mM/60 µL) by measuring the weight of the animals suffering from a glioma.

Rats were also closely monitored for their weight loss, an indirect indicator of tumor growth reflecting the therapeutic effect of the injected agent. Daily weighing of animals showed that the weight loss of NFL-TBS$_{40-63}$ treated animals was significantly lower when compared to untreated animals (FIG. 11).

All together, the above-presented results highlight the significant capacity of the NFL-TBS$_{40-63}$ peptide to:

a) penetrate in glioma cells in vivo, when injected intratumorally, b) induce apoptosis of the glioma cells in which it penetrates, c) avoid affecting the other non-tumoral regions of the brain, d) inhibit the progression of glioma in vivo, by mean of only one injection.

3.4. Use of NFL-TBS2 Peptide for Targeting Nanocapsules to Glioma Cells

Figure 14:
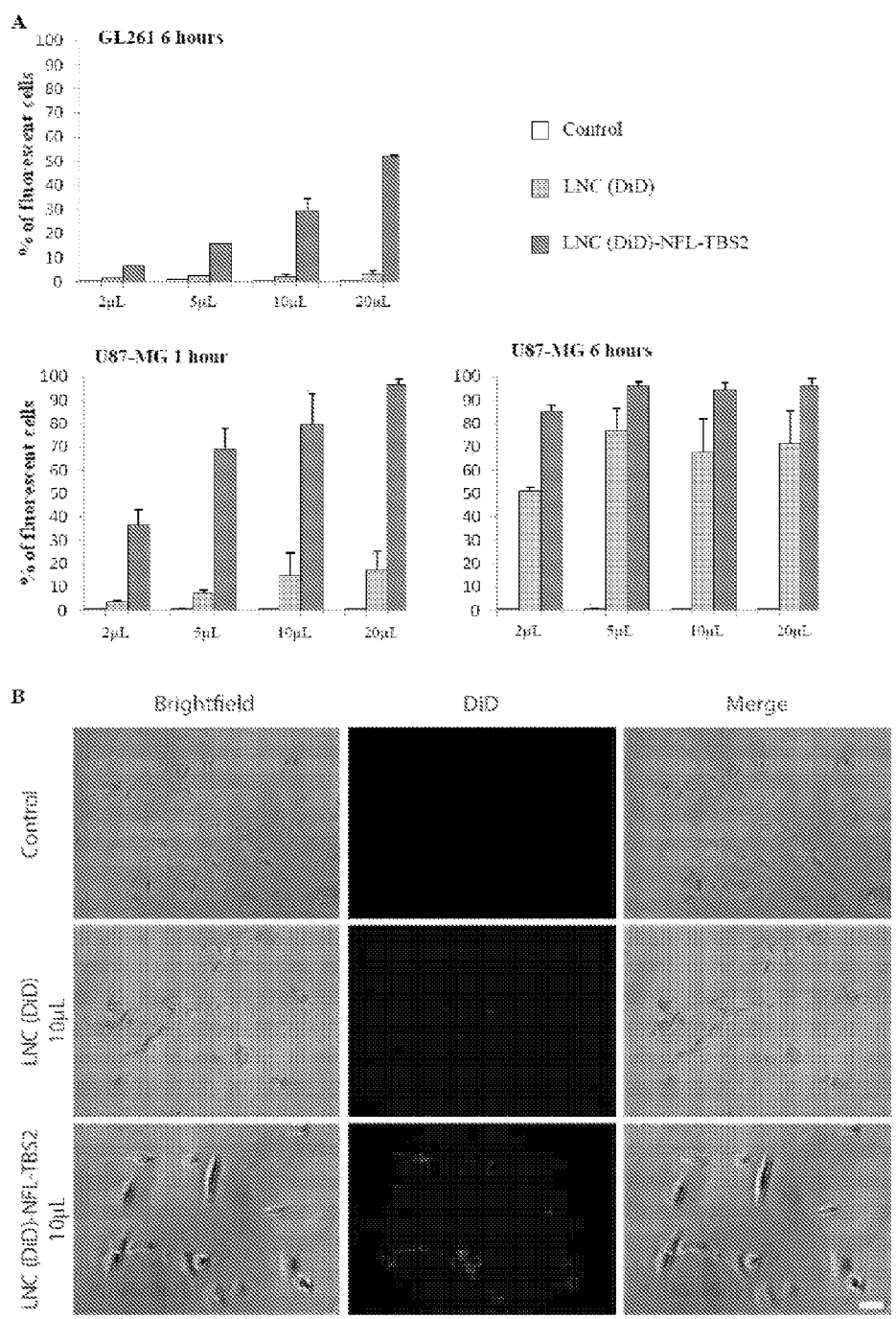
FIG. 14 shows that NFL-TBS2 peptide can be used to improve the targeted uptake of lipid nanocapsules (LNC) in glioma cells. GL261 cells were treated for 6 hours, and U87-MG cells for 1 or 6 hours with different dilution of LNC containing a lipophilic fluorochrome (DiD). Cell fluorescence was measured by FACS (A). Images of living GL261 cells show higher fluorescence in cells treated with 10 µL of LNC (DiD) coupled to NFL-TBS2 peptide for 6 hours than those treated with LNC (DiD) alone (B). LNC (DiD)-NFL-TBS2 are both incorporated in GL261 cells (top line) and T98G human glioma cells (bottom line) (C, White bar=25 µm). When LNC (DiD)-NFL-TBS2 are administered in C57B1/6 mice with GL261 tumor cells, they are sequestered in the tumor tissue (on the right) and not in the healthy tissue (on the left) (D).
Figure 14C:
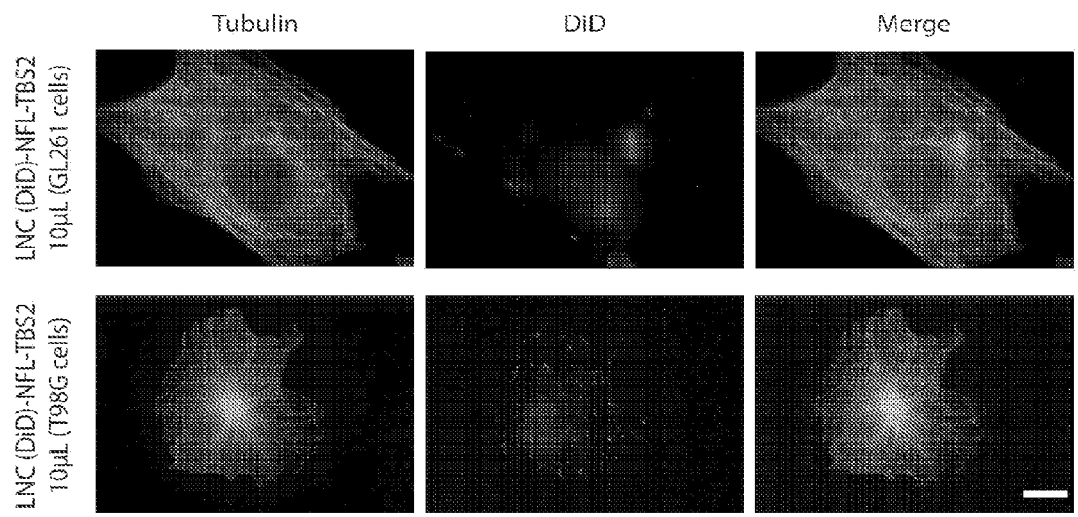

Lipid nanocapsules containing a lipophilic flurorochrome were obtained and coupled or not with the NFL-TBS2 peptide. Three glioma cell lines (GL261, T98G and U87-MG cells) were treated for 1 or 6 hour(s) with different dilution of LNC containing the lipophilic fluorochrome (DiD) coupled or not with the NFL-TBS2 peptide. Improved targeting of the glioma cell lines with the NFL-TBS2-coupled LNC was observed by FACS (FIG. 14A), and by confocal microscopy on living cells (FIG. 14B) or fixed cells (FIG. 14C).

Figure 14D:
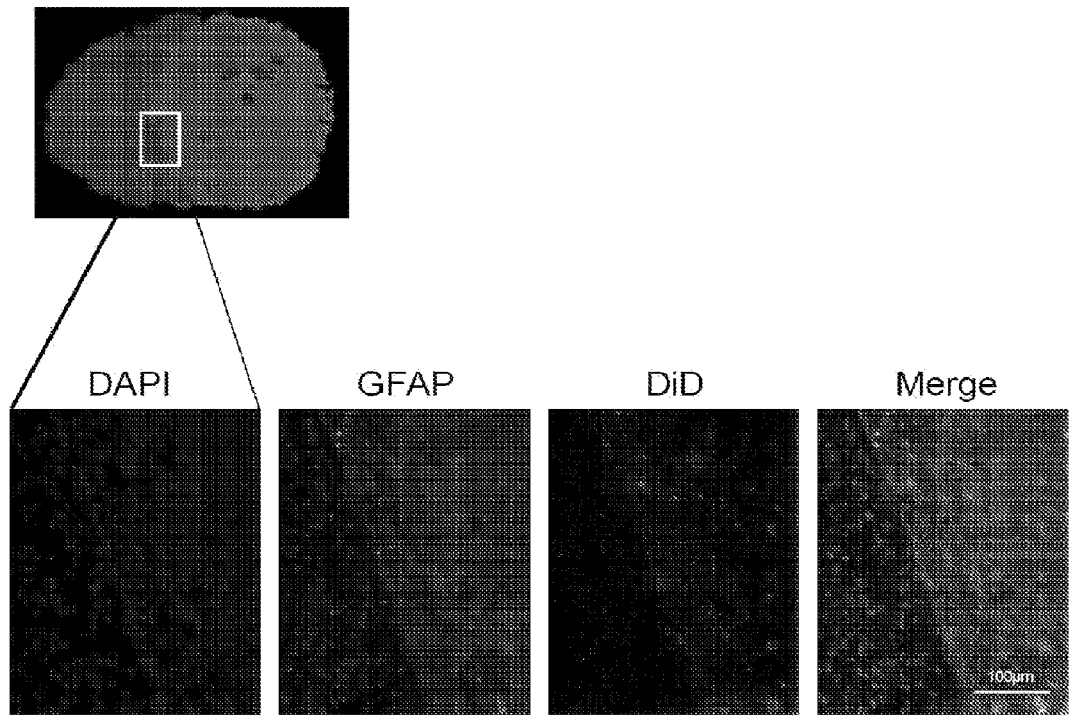

In vivo experiments have also been performed in C57B1/6 mice bearing a GL261 tumor. To detect the tumor, serial sections of the brain were labelled with DAPI or using an antibody against GFAP (Glial Fibrillary Acid Protein), the intermediate filament highly expressed in glial tumors like glioblastoma. Importantly, when LNC (DiD)-NFL-TBS2 are administered intracerebrally by stereotaxic injection in the tumor-bearing mice, the LNC are able to reach the glioma cells (see on the right of the image on FIG. 14D) and they remain sequestered in the tumor tissue (they are not observed in the healthy tissue).

These results thus allow considering the NFL-TBS$_{40-63}$ peptide as a very promising tool for treating glioma tumor, either in animals or in human beings. Besides its therapeutic efficiency in reducing tumor size, the NFL-TBS$_{40-63}$ peptide does not show the strong neurotoxicity usually associated with this kind of (microtubule-targeting) drugs. It is therefore embodied as being the future therapeutic agent for treating patients suffering from glioma.

BIBLIOGRAPHIC REFERENCES

Barth, R F (1998) *J. Neurooncol* 36: 91-102
Bocquet A, et al (2009) *Neurosci* 29: 11043-11054.
Budman D. R. (1997). *Cancer Invest* 15: 475-490.
Cavaletti G, et al (1997). *Neurotoxicology* 18: 137-145.
Dumontet C., (1999). *J Clin Oncol* 17: 1061-1070
Gottesman M M and Pastan I (1993). *Annu Rev Biochem* 62: 385-427.
Heurtault B., et al., *Pharm. Res.* 19 (2002), pp. 875-880
Hofer S and Herrmann R (2001). *J Cancer Res Clin Oncol* 127: 91-95.
Kaech S. and Banker G. (2006) *Nat Protoc.* 2006; 1(5): 2406-15
McCarthy K D and de Vellis J (1980). *J Cell Biol* 85: 890-902.
Mollinedo F. et al., (2003). *Apoptosis* 8: 413-450.
Ray J, et al. (1993) *PNAS* USA. April 15; 90(8):3602-6.
Redgate et al. (1991). *Laboratory animal science* 41: 269-73.
Rocchetti et al (2007). *European Journal of Cancer* 2007, vol 43, n°12, p 1862-1868
Schrijvers D. et al. (1998). *Curr Opin Oncol* 10: 233-241.
Wang T H, et al. (2000). *Cancer* 88:2619-2628.

---

The invention claimed is:

1. A method for treating malignant glioma, comprising administering to a subject in need thereof an effective amount of a pharmaceutical composition comprising at least an isolated amino acid sequence comprising:
   the neurofilament light chain-tubulin-binding site (NFL-TBS)40-63 peptide (SEQ ID NO: 1),
   the peptide of SEQ ID NO:3,
   a biologically active fragment thereof comprising at least 18 successive amino acids of SEQ ID NO:1 or of SEQ ID NO:3,
   a biologically active variant thereof having at least 95% of identity with SEQ ID NO:1 or with SEQ ID NO:3, or
   any combination thereof,
wherein said malignant glioma is a brain malignant glioma.

2. The method according to claim 1, wherein said brain malignant glioma is selected from the group consisting of: anaplastic astrocytoma (AA), glioblastoma multiform (GBM), anaplastic oligodendroglioma (AO), and anaplastic oligoastrocytoma (AOA).

3. The method according to claim 1, wherein said brain malignant glioma is a glioblastoma multiform (GBM).

4. The method according to claim 1, wherein said isolated amino acid sequence is administered to human beings at a dose that is comprised between about 0.07 and 0.7 millimole.

5. The method according to claim 1, wherein said isolated amino acid sequence consists of:
   the NFL-TBS40-63 peptide (SEQ ID NO: 1),
   the peptide of SEQ ID NO:3,
   a biologically active fragment thereof comprising at least 18 successive amino acids of SEQ ID NO:1 or of SEQ ID NO:3,
   a biologically active variant thereof having at least 95% of identity with SEQ ID NO:1 or with SEQ ID NO:3, or
   any combination thereof.

* * * * *

SEQUENCE LISTING

```
<160> NUMBER OF SEQ ID NOS: 3

<210> SEQ ID NO 1
<211> LENGTH: 24
<212> TYPE: PRT
<213> ORGANISM: artificial
<220> FEATURE:
<223> OTHER INFORMATION: TBS motif of the human light chain
      neurofilament protein, amino acids

<400> SEQUENCE: 1

Tyr Ser Ser Tyr Ser Ala Pro Val Ser Ser Leu Ser Val Arg Arg
1               5                   10                  15

Ser Tyr Ser Ser Ser Ser Gly Ser
            20

<210> SEQ ID NO 2
<211> LENGTH: 24
<212> TYPE: PRT
<213> ORGANISM: artificial
<220> FEATURE:
<223> OTHER INFORMATION: artificial scrambled peptide (NFL-SCR)

<400> SEQUENCE: 2

Ser Leu Gly Ser Pro Ser Ser Val Arg Ala Ser Tyr Ser Ser Ser
1               5                   10                  15

Arg Ser Tyr Val Tyr Ser Ser Ser
            20

<210> SEQ ID NO 3
<211> LENGTH: 20
<212> TYPE: PRT
<213> ORGANISM: artificial
<220> FEATURE:
<223> OTHER INFORMATION: TBS motif of the quail light chain
```

```
                neurofilament protein

<400> SEQUENCE: 3

Tyr Ser Ser Ser Ala Pro Val Ser Ser Val Arg Arg Ser Tyr Ser
1               5                   10                  15

Ser Ser Gly Ser
            20
```